United States Patent
Sin et al.

(10) Patent No.: US 11,853,042 B2
(45) Date of Patent: Dec. 26, 2023

(54) PART, SENSOR, AND METROLOGY DATA INTEGRATION

(71) Applicant: Applied Materials, Inc., Santa Clara, CA (US)

(72) Inventors: Garrett Ho-Yee Sin, Sunnyvale, CA (US); Sidharth Bhatia, Santa Cruz, CA (US); Katty Marie Lydia Gamon Guyomard, Los Altos, CA (US); Shawyon Jafari, Sunnyvale, CA (US); Heng-Cheng Pai, Cupertino, CA (US); Pramod Nambiar, Sunnyvale, CA (US); Paul Lukas Brillhart, Pleasanton, CA (US); Ilker Durukan, San Jose, CA (US)

(73) Assignee: Applied Materials, Inc., Santa Clara, CA (US)

( * ) Notice: Subject to any disclaimer, the term of this patent is extended or adjusted under 35 U.S.C. 154(b) by 116 days.

(21) Appl. No.: 17/177,978

(22) Filed: Feb. 17, 2021

(65) Prior Publication Data

US 2022/0260978 A1  Aug. 18, 2022

(51) Int. Cl.
*G05B 19/418* (2006.01)
*G06N 20/00* (2019.01)
(Continued)

(52) U.S. Cl.
CPC ....... *G05B 19/41875* (2013.01); *G01N 33/00* (2013.01); *G06F 30/398* (2020.01);
(Continued)

(58) Field of Classification Search
None
See application file for complete search history.

(56) References Cited

U.S. PATENT DOCUMENTS

| 6,751,518 B1 | 6/2004 | Sonderman et al. |
| 7,321,993 B1 * | 1/2008 | Markle ............. G05B 23/0235 714/48 |

(Continued)

FOREIGN PATENT DOCUMENTS

| CN | 101621016 A | 1/2010 |
| TW | 201435969 A | 9/2014 |

(Continued)

OTHER PUBLICATIONS

International Search Report and Written Opinion dated Jun. 11, 2020, on application No. PCT/US2020/018673.

(Continued)

*Primary Examiner* — Jason Lin
(74) *Attorney, Agent, or Firm* — Lowenstein Sandler LLP

(57) ABSTRACT

A method includes receiving part data associated with a corresponding part of substrate processing equipment, sensor data associated with one or more corresponding substrate processing operations performed by the substrate processing equipment to produce one or more corresponding substrates, and metrology data associated with the one or more corresponding substrates produced by the one or more corresponding substrate processing operations performed by the substrate processing equipment that includes the corresponding part. The method further includes generating sets of aggregated part-sensor-metrology data including a corresponding set of part data, a corresponding set of sensor data, and a corresponding set of metrology data. The method further includes causing analysis of the sets of aggregated part-sensor-metrology data to generate one or more outputs to perform a corrective action associated with the corresponding part of the substrate processing equipment.

17 Claims, 7 Drawing Sheets

(51) Int. Cl.
*G01N 33/00* (2006.01)
*G06F 30/398* (2020.01)
*G06F 119/22* (2020.01)
*G06F 119/18* (2020.01)

(52) U.S. Cl.
CPC ..... *G06N 20/00* (2019.01); *G01N 2033/0095* (2013.01); *G05B 2219/31264* (2013.01); *G05B 2219/32179* (2013.01); *G05B 2219/45031* (2013.01); *G06F 2119/18* (2020.01); *G06F 2119/22* (2020.01)

(56) References Cited

U.S. PATENT DOCUMENTS

| | | | | |
|---|---|---|---|---|
| 7,873,585 | B2 * | 1/2011 | Izikson | G03F 7/70625 706/21 |
| 2003/0014145 | A1 * | 1/2003 | Reiss | G05B 23/0286 700/121 |
| 2003/0182252 | A1 | 9/2003 | Beinglass et al. | |
| 2003/0229410 | A1 * | 12/2003 | Smith | H01L 21/3212 700/109 |
| 2004/0167655 | A1 * | 8/2004 | Middlebrooks | G05B 13/048 700/121 |
| 2006/0047356 | A1 * | 3/2006 | Funk | H01L 22/20 700/121 |
| 2007/0100487 | A1 | 5/2007 | Cheng et al. | |
| 2008/0262769 | A1 * | 10/2008 | Kadosh | G01R 31/2894 702/123 |
| 2008/0276136 | A1 | 11/2008 | Lim et al. | |
| 2011/0112678 | A1 * | 5/2011 | Hsu | H01L 21/67253 700/121 |
| 2013/0060354 | A1 * | 3/2013 | Choi | G05B 19/41875 700/51 |
| 2013/0110263 | A1 | 5/2013 | Schulze et al. | |
| 2013/0110276 | A1 * | 5/2013 | Cheng | G06F 30/36 700/121 |
| 2013/0310966 | A1 * | 11/2013 | MacNaughton | G03F 7/70616 700/121 |
| 2014/0149296 | A1 | 5/2014 | Chang et al. | |
| 2015/0253373 | A1 * | 9/2015 | Callegari | H01L 22/20 702/58 |
| 2016/0148850 | A1 * | 5/2016 | David | G03F 7/70625 355/53 |
| 2016/0342147 | A1 | 11/2016 | Iskandar et al. | |
| 2017/0023867 | A1 | 1/2017 | Staals et al. | |
| 2018/0358271 | A1 * | 12/2018 | David | H01L 22/14 |
| 2019/0138415 | A1 | 5/2019 | Chen et al. | |
| 2019/0286075 | A1 * | 9/2019 | Yennie | B24B 37/013 |
| 2019/0369503 | A1 * | 12/2019 | Ypma | G05B 19/41875 |
| 2020/0226742 | A1 | 7/2020 | Sawlani et al. | |
| 2020/0264335 | A1 | 8/2020 | Bhatia et al. | |
| 2021/0018902 | A1 | 1/2021 | Yennie et al. | |
| 2021/0389677 | A1 * | 12/2021 | Lin | G05B 19/41875 |

FOREIGN PATENT DOCUMENTS

| | | |
|---|---|---|
| TW | I644190 B | 9/2014 |
| TW | 201817539 B | 1/2016 |
| TW | 201705034 A | 2/2017 |
| TW | 201712440 A | 4/2017 |
| TW | 201817539 A | 5/2018 |
| TW | I644190 B | 12/2018 |
| WO | 2004012230 A1 | 2/2004 |
| WO | 2020172186 A1 | 8/2020 |
| WO | 2020205339 A1 | 10/2020 |
| WO | 2022177805 A | 8/2022 |
| WO | 2022177805 A1 | 8/2022 |

OTHER PUBLICATIONS

International Search Report and Written Opinion dated May 23, 2022, on application No. PCT/US2022/016003.
Taiwan Search Report received form Taiwan Application No. 109105293, dated Mar. 14, 2022.

* cited by examiner

PART, SENSOR, AND METROLOGY DATA INTEGRATION

TECHNICAL FIELD

The present disclosure relates to data integration, and, more particularly, part, sensor, and metrology data integration.

BACKGROUND

Products are produced by performing one or more manufacturing processes using manufacturing equipment. Manufacturing equipment is made of multiple parts. Faulty products can be caused by suboptimal parts and by suboptimal manufacturing processes.

SUMMARY

The following is a simplified summary of the disclosure in order to provide a basic understanding of some aspects of the disclosure. This summary is not an extensive overview of the disclosure. It is intended to neither identify key or critical elements of the disclosure, nor delineate any scope of the particular implementations of the disclosure or any scope of the claims. Its sole purpose is to present some concepts of the disclosure in a simplified form as a prelude to the more detailed description that is presented later.

In an aspect of the disclosure, a method includes receiving a plurality of sets of part data, each of the plurality of sets of part data being associated with a corresponding part of substrate processing equipment. The method further includes receiving a plurality of sets of sensor data, each of the plurality of sets of sensor data being associated with one or more corresponding substrate processing operations performed by the substrate processing equipment to produce one or more corresponding substrates. The method further includes receiving a plurality of sets of metrology data, each of the plurality of sets of metrology data being associated with the one or more corresponding substrates produced by the one or more corresponding substrate processing operations performed by the substrate processing equipment that comprises the corresponding part. The method further includes generating a plurality of sets of aggregated part-sensor-metrology data, each of the plurality of sets of aggregated part-sensor-metrology data comprising a corresponding set of part data, a corresponding set of sensor data, and a corresponding set of metrology data. The method further includes causing analysis of the plurality of sets of aggregated part-sensor-metrology data to generate one or more outputs to perform a corrective action associated with the corresponding part of the substrate processing equipment.

In an aspect of the disclosure, a system includes a memory and a processing device coupled to the memory. The processing device is to receive a plurality of sets of part data, each of the plurality of sets of part data being associated with a corresponding part of substrate processing equipment. The processing device is further to receive a plurality of sets of sensor data, each of the plurality of sets of sensor data being associated with one or more corresponding substrate processing operations performed by the substrate processing equipment to produce one or more corresponding substrates. The processing device is further to receive a plurality of sets of metrology data, each of the plurality of sets of metrology data being associated with the one or more corresponding substrates produced by the one or more corresponding substrate processing operations performed by the substrate processing equipment that comprises the corresponding part. The processing device is further to generate a plurality of sets of aggregated part-sensor-metrology data, each of the plurality of sets of aggregated part-sensor-metrology data comprising a corresponding set of part data, a corresponding set of sensor data, and a corresponding set of metrology data. The processing device is further to cause analysis of the plurality of sets of aggregated part-sensor-metrology data to generate one or more outputs to perform a corrective action associated with the corresponding part of the substrate processing equipment.

In an aspect of the disclosure, a non-transitory computer readable medium having instructions stored thereon, which, when executed by a processing device, cause the processing device to receive a plurality of sets of part data, each of the plurality of sets of part data being associated with a corresponding part of substrate processing equipment. The processing device is further to receive a plurality of sets of sensor data, each of the plurality of sets of sensor data being associated with one or more corresponding substrate processing operations performed by the substrate processing equipment to produce one or more corresponding substrates. The processing device is further to receive a plurality of sets of metrology data, each of the plurality of sets of metrology data being associated with the one or more corresponding substrates produced by the one or more corresponding substrate processing operations performed by the substrate processing equipment that comprises the corresponding part. The processing device is further to generate a plurality of sets of aggregated part-sensor-metrology data, each of the plurality of sets of aggregated part-sensor-metrology data comprising a corresponding set of part data, a corresponding set of sensor data, and a corresponding set of metrology data. The processing device is further to cause analysis of the plurality of sets of aggregated part-sensor-metrology data to generate one or more outputs to perform a corrective action associated with the corresponding part of the substrate processing equipment.

BRIEF DESCRIPTION OF THE DRAWINGS

The present disclosure is illustrated by way of example, and not by way of limitation in the figures of the accompanying drawings.

DETAILED DESCRIPTION

Figure 1:
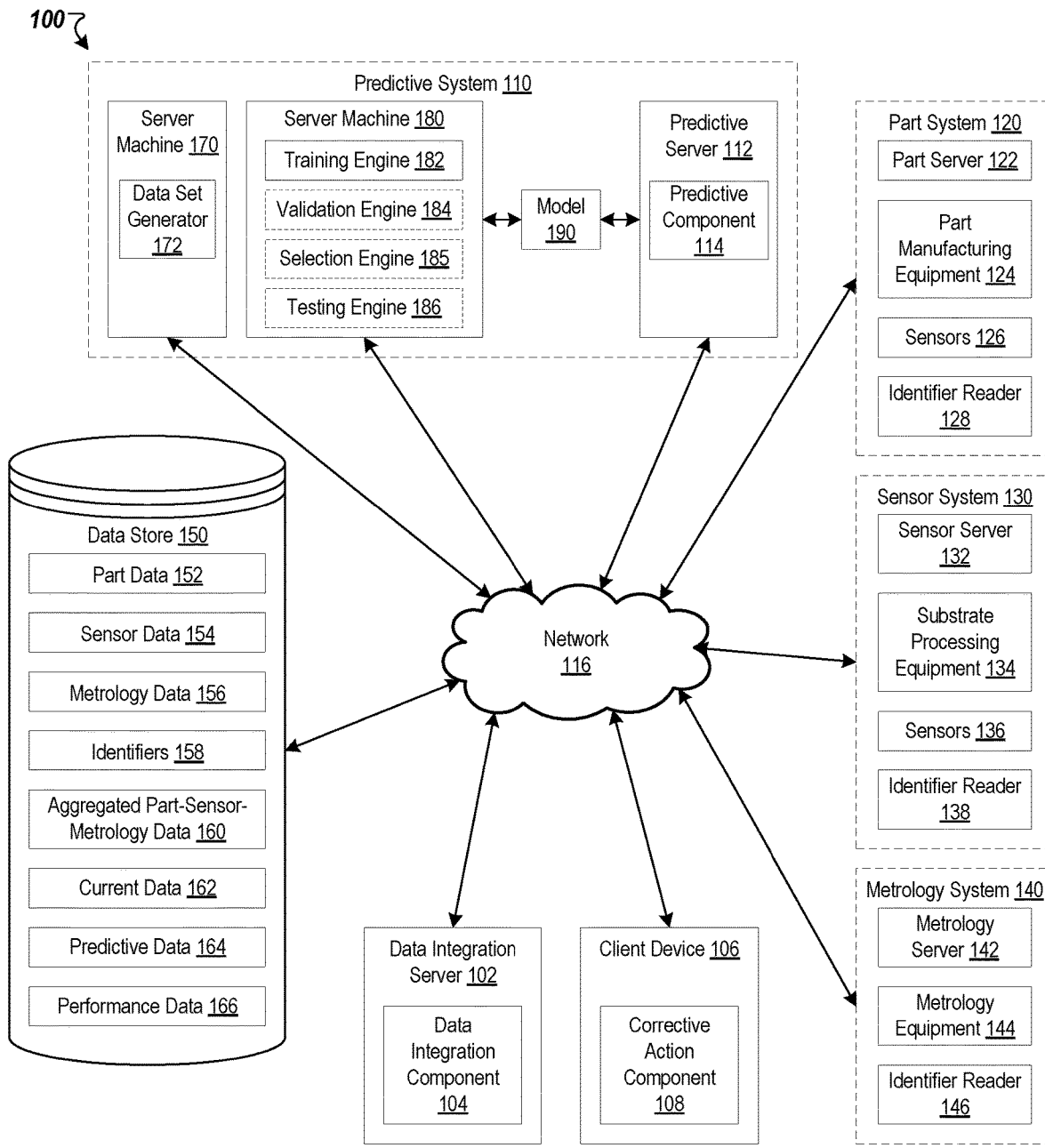
FIG. 1 is a block diagram illustrating an exemplary system architecture, according to certain embodiments.

Described herein are technologies directed to part, sensor, and metrology data integration.

Manufacturing equipment is used to generate products. For example, substrate processing equipment is used to produce substrates. Substrate processing equipment is made of parts (e.g., that are made by part manufacturing equipment). Substrate processing equipment performs substrate processing equipment. Performance data of the substrates is determined. For example, metrology equipment is used to determine metrology data (e.g., measurements, dimensions, material properties, imaging data, etc.) of substrates produced via substrate processing operations by substrate processing equipment. Substrates with performance data that does not meet threshold values (e.g., does not meet threshold dimensions, etc.) may be a result of one or more suboptimal parts of the substrate processing equipment and/or one or more suboptimal parameters of the substrate processing operations (e.g., temperature, pressure, flow rate, etc.).

Conventionally, improving products is a manual, trial-and-error process. Responsive to performance data of a substrate not meeting threshold values, conventionally a user replaces one or more parts of the substrate processing equipment and/or changes the manufacturing parameters of one or more substrate processing operations. This is repeated until performance data of a substrate meets threshold values. This is time consuming, wastes parts, wastes substrates, decreases yield, and may not result in substrates of optimal performance.

Conventionally, part data, sensor data, and metrology data are stored in different locations in different formats and may not be readily accessible by a user. This prevents data analysis of the different types of data. In some cases, blame of poor product performance to be erroneously directed to one or more of the part manufacturing, part installation, substrate processing operations, maintenance, etc. when the cause of the poor product performance is actually caused by something different.

The systems and methods disclosed herein are associated with part, sensor, and metrology data integration. Part data, sensor data, and metrology data are identified. The part data is associated with a corresponding part of substrate processing equipment. For example, part data can include dimensions, material properties, storage data, transportation data, environmental data, etc. The sensor data is associated with substrate processing operations performed by the substrate processing equipment to produce substrates. For example, sensor data can include temperature, pressure, flow rate, etc. The metrology data is associated with substrates produced by the substrate processing operations performed by substrate processing equipment that include the parts. The metrology data can include measurements of the substrates, images of the substrates, etc.

The part data, sensor data, and metrology data are aggregated (e.g., linked, integrated, etc.) to form aggregated part-sensor-metrology data. In some embodiments, each of the part data, sensor data, and the metrology data include identifiers and common portions between identifiers are used to identify part-sensor-metrology matches to generate sets of aggregated part-sensor-metrology data.

Analysis of the sets of aggregated part-sensor-metrology data is caused to generate outputs. The outputs are used to perform a corrective action associated with a part of the substrate processing equipment. The corrective action can include updating design of the part, quality of the part, dimensions of the part, feature layout of the part, part manufacturing operations to produce the part, performing root cause analysis to determine updates to the part or the substrate processing operations, etc. In some embodiments, causing analysis of the aggregated part-sensor-metrology data includes storing the aggregated part-sensor-metrology data. In some embodiments, causing analysis of the aggregated part-sensor-metrology data includes training a machine learning model using data input of the aggregated part-sensor-metrology data to generate a trained machine learning model. In some embodiments, causing analysis of the aggregated part-sensor-metrology data includes providing the aggregated part-sensor-metrology data as data input to a trained machine learning model to receive the outputs to perform a corrective action associated with the part of the substrate processing equipment.

Aspects of the present disclosure result in technological advantages compared to conventional solutions. The present disclosure is used for determining a corrective action without the conventional manual trial and error. This reduces time, reduces waste of parts, reduces waste of products, and increases yield. The present disclosure causes analysis of part, sensor, and metrology data to determine corrective actions from part manufacturing and substrate manufacturing parameters compared to conventional solutions that only considers a portion of the data. The use of aggregated part-sensor-metrology data in the present disclosure causes corrective actions to be performed more rapidly and with less errors that conventional approaches. The present disclosure may be used to determine impact of part variability and/or run variability on production of substrates (e.g., to control tool operation to improve on-wafer performance) which may not be determined using conventional solutions. The present disclosure may be used to correlate manufacturing data of a part with on-wafer performance to identify good versus bad parts and improve the part manufacturing process to increase the number of parts that have good on-wafer performance. This may result in better parts, better substrates, and greater yield than conventional solutions.

Although some embodiments of the present disclosure describe integration of part data, sensor data, and metrology data, in some embodiments, different combinations of data may be used. For example, aggregated part-sensor data, aggregated part-metrology data, aggregated sensor-metrology data, part manufacturing data aggregated with other data, part installation data aggregated with other data, and/or the like may be used.

Although some embodiments of the present disclosure describe part data, sensor data, and metrology data associated with substrate processing equipment, in some embodiments, the part data, sensor data, and metrology data can correspond to other types of equipment (e.g., manufacturing equipment) used to produce products.

FIG. 1 is a block diagram illustrating an exemplary system architecture of system 100, according to certain embodiments. The system 100 includes a data integration server 102, a client device 106, a part system 120, a sensor system 130, a metrology system 140, a predictive server 112, and a data store 150. The predictive server 112 may be part of a predictive system 110. The predictive system 110 may further include server machines 170 and 180.

The part system 120 may include a part server 122, part manufacturing equipment 124, sensors 126, and an identifier reader 128 (e.g., to read a part number and/or serial number of a part). The sensor system 130 includes a sensor server 132 (e.g., field service server (FSS) at a manufacturing facility), substrate processing equipment 134, sensors 136, and identifier reader 138 (e.g., front opening unified pod (FOUP) radio frequency identification (RFID) reader for sensor system 130). The metrology system 140 includes a metrology server 142 (e.g., metrology database, metrology folders, etc.), metrology equipment 144, and identifier reader 146 (e.g., FOUP RFID reader for metrology system 140).

Sensors 126 may provide part data 152 (e.g., manufacturing parameters of part manufacturing equipment 124, measurements of the part, etc.) associated with a part produced by the manufacturing equipment 124.

The part data 152 may include a value of one or more of temperature (e.g., heater temperature), spacing (SP), pressure, high frequency radio frequency (HFRF), voltage, electrical current, flow, power, voltage, etc. Part data 152 may be associated with or indicative of manufacturing parameters such as hardware parameters (e.g., settings or components (e.g., size, type, etc.) of the part manufacturing equipment 124) or process parameters of the part manufacturing equipment 124. The part data 152 may be provided while the part manufacturing equipment 124 is performing manufacturing operations (e.g., equipment readings when manufacturing parts). The part data 152 may be different for each part. The parts may be used in substrate processing equipment 134. For example, a part may be a showerhead, pedestal, heater, rubber membrane to apply pressure to a first side of a substrate when performing substrate processing of a second side of the substrate, an electrostatic chuck, etc.

Sensors 136 may provide sensor data 154 (e.g., manufacturing parameters of substrate processing equipment 134, etc.) associated with a substrate produced by the substrate processing equipment 134. The sensor data 154 may include a value of one or more of temperature (e.g., heater temperature), spacing (SP), pressure, high frequency radio frequency (HFRF), voltage of electrostatic chuck (ESC), electrical current, flow, power, voltage, etc. Sensor data 154 may be associated with or indicative of manufacturing parameters such as hardware parameters (e.g., settings or components (e.g., size, type, etc.) of the substrate processing equipment 134) or process parameters of the substrate processing equipment 134. The sensor data 154 may be provided while the substrate processing equipment 134 is performing substrate processing operations (e.g., equipment readings when processing substrates). The sensor data 154 may be different for each product (e.g., each substrate).

Metrology equipment 144 may provide metrology data 156 (e.g., measurements, material properties, storage information, environmental conditions, etc.) of a substrate produced by the substrate processing equipment 134. The metrology equipment 144 may provide metrology data 156 (e.g., property data of substrates) associated with substrates produced by the substrate processing equipment 134. The metrology data 156 may include a value of one or more of film property data (e.g., wafer spatial film properties), dimensions (e.g., thickness, height, etc.), dielectric constant, dopant concentration, density, defects, etc. The metrology data 156 may be of a finished or semi-finished product. The metrology data 156 may be different for each product (e.g., each substrate).

The identifier reader 128, 138, and/or 146 may provide an identifier 158. In some embodiments, identifier reader 128, 138, and/or 138 may be an RFID reader (e.g., FOUP RFID reader, carrier RFID reader), an imaging device (e.g., barcode reader, etc.), and/or the like. The identifier 158 includes one or more of an indication of a carrier (e.g., carrier identifier), indication of a product (e.g., which substrate in the carrier, order of the substrates), an indication of a timestamp (e.g., date, time, etc.).

In some embodiments, the identifier reader 128 of the part system 120 may provide an identifier 158 associated with one or more of the manufacturing of the part, the installation of the part, the storage of the part, the transportation of the part, etc.

In some embodiments, identifier reader 138 (e.g., FOUP RFID reader) of the sensor system 130 may provide an identifier 158 (e.g., carrier identifier, such as a FOUP identifier, substrate carrier identifier, slot identifier, etc.).

In some embodiments, identifier reader 146 (e.g., FOUP RFID reader) of the metrology system may provide an identifier 158 (e.g., carrier identifier, such as a FOUP identifier, substrate carrier identifier, slot identifier, etc.).

In some embodiments, a product carrier (e.g., FOUP, wafer carrier) may transfer substrates from the substrate processing equipment 134 to the metrology equipment 144. The substrates may maintain the same order (e.g., same location in the FOUP or wafer carrier) in the sensor system 130 and in the metrology system 140. For example, substrates may be loaded into and out of the substrate processing equipment 134 (e.g., for performing substrate processing of the substrates and providing sensor data 154 via sensor server 132) in the same order as they are loaded into and out of metrology equipment 144 (e.g., for providing metrology data 156 via metrology system 140). In some embodiments, the identifier 158 provided by the identifier reader 138 (e.g., FOUP ID associated with sensor system 130) and the identifier reader 138 provided by the identifier reader 146 (e.g., FOUP ID associated with metrology system 140) that correspond to the same products are associated with the same product carrier (e.g., the same FOUP) and/or carrier identifier (e.g., the sensor carrier identifier and the metrology carrier identifier are the same).

The data integration server 102, client device 106, part system 120 (e.g., part server 122, part manufacturing equipment 124, sensors 126, identifier reader 128, etc.), sensor system 130 (e.g., sensor server 132, substrate processing equipment 134, sensors 136, identifier reader 138, etc.), metrology system 140 (e.g., metrology server 142, metrology equipment 144, identifier reader 146, etc.), predictive server 112, data store 150, server machine 170, and server machine 180 may be coupled to each other via a network 116 for generating aggregated part-sensor-metrology data 160 to perform corrective actions. In some embodiments, network 116 is a public network that provides client device 106 with access to the predictive server 112, data store 150, and other publically available computing devices. In some embodiments, network 116 is a private network that provides data integration server 102 access to the sensor system 130, metrology system 140, data store 150, and other privately available computing devices and that provides client device 106 access to the predictive server 112, data store 150, and other privately available computing devices. Network 116 may include one or more wide area networks (WANs), local area networks (LANs), wired networks (e.g., Ethernet network), wireless networks (e.g., an 802.11 network or a Wi-Fi network), cellular networks (e.g., a Long Term Evolution (LTE) network), routers, hubs, switches, server computers, cloud computing networks, and/or a combination thereof.

The client device 106 may include a computing device such as a personal computer (PC), desktop computer, laptop, mobile phone, smart phone, tablet computer, netbook computer, etc. The client device 106 may include a corrective action component 108. Corrective action component 108 may receive user input (e.g., via a graphic user interface (GUI) displayed via the client device 106) of an indication associated with substrate processing equipment 134 (e.g., a part of substrate processing equipment, substrates produced by the substrate processing equipment, etc.). In some embodiments, the corrective action component 108 transmits the indication to the predictive system 110, receives output (e.g., predictive data 164) from the predictive system 110, determines a corrective action based on the output, and causes the corrective action to be implemented. Client device 106 may include an operating system that allows users to one or more of generate, view, or edit data (e.g., indication associated with a part, substrate processing equipment 134, substrate, corrective actions associated with the part, etc.).

Corrective actions may be associated with one or more of computational process control (CPC), statistical process control (SPC), automatic process control (APC), preventative operative maintenance, design optimization, updating of manufacturing parameters, feedback control, machine learning modification, etc.

In some embodiments, the corrective action is providing an alert (e.g., an alarm to stop or not perform the manufacturing process if the predictive data 164 indicates the part or product is to have poor performance, such as a hole of the part is predicted to not be round). In some embodiments, the corrective action is providing feedback control (e.g., modifying a manufacturing parameter, such as to slow down the drill removal responsive to the predictive data 164 indicating the hole is predicted to not be round). In some embodiments, the corrective action is providing machine learning (e.g., modifying one or more manufacturing parameters, such as drill rotation, rate of insertion, rate of removal, etc. based on the predictive data 164).

In some embodiments, the corrective action is causing updates to one or more manufacturing parameters. Manufacturing parameters may include hardware parameters (e.g., replacing components, using certain components, etc.) and/or process parameters (e.g., temperature, pressure, flow, rate, etc.). In some embodiments, the corrective action is causing preventative operative maintenance (e.g., replace, process, clean, etc. components of the part manufacturing equipment 124 and/or substrate processing equipment 134). In some embodiments, the corrective action is causing design optimization (e.g., updating manufacturing parameters, manufacturing processes, part design, substrate processing equipment 134, etc. for an optimized product).

The data integration server 102, predictive server 112, sensor server 132, metrology server 142, server machine 170, and server machine 180 may each include one or more computing devices such as a rackmount server, a router computer, a server computer, a PC, a mainframe computer, a laptop computer, a tablet computer, a desktop computer, graphics processing unit (GPU), accelerator application-specific integrated circuit (ASIC) (e.g., tensor processing unit (TPU)), etc.

The data integration server 102 may include a data integration component 104. The data integration component 104 may receive sets of part data 152 (e.g., from part server 122, from the data store 150), sets of sensor data 154 (e.g., from the sensor server 132, from the data store 150), and sets of metrology data 156 (e.g., from the metrology server 142, from the data store 150), determine part-sensor-metrology matches between the sets of part data 152, the sets of sensor data 154, and the sets of metrology data 156, generate sets of aggregated part-sensor-metrology data 160 based on the sensor-metrology matches, and store the sets of aggregated part-sensor-metrology data 160 in the data store 150.

The predictive server 112 may include a predictive component 114. In some embodiments, the predictive component 114 may retrieve aggregated part-sensor-metrology data 160 from the data store and generate output (e.g., predictive data 164) for performing a corrective action associated with a part of the substrate processing equipment 134 based on the aggregated part-sensor-metrology data 160. In some embodiments, the predictive component 114 may use a trained machine learning model 190 to determine the output for performing the corrective action. The trained machine learning model 190 may be trained using the aggregated part-sensor-metrology data 160 to learn key process and hardware parameters. Generating, by the trained machine learning model 190, output for performing corrective action may include prescribing, by the trained machine learning model 190, optimal operating conditions (e.g., process parameters) and/or space (e.g., hardware parameters). In some embodiments, the predictive component 114 determines predictive data 164 for performing corrective action by providing current data 162 (e.g., current aggregated part-sensor-metrology data 160) into the trained machine learning model 190, obtaining output from the trained machine learning model 190, and determining predictive data 164 based on the output.

Data store 150 may be memory (e.g., random access memory), a drive (e.g., a hard drive, a flash drive), a database system, or another type of component or device capable of storing data. Data store 150 may include multiple storage components (e.g., multiple drives or multiple databases) that may span multiple computing devices (e.g., multiple server computers). The data store 150 may store part data 152, sensor data 154, metrology data 156, identifiers 158, aggregated part-sensor-metrology data 160, current data 162, predictive data 164 (e.g., predictive performance data), and performance data 166. The part data 152, sensor data 154, metrology data 156, and aggregated part-sensor-metrology data 160 may include historical data (e.g., for training the machine learning model 190). The current data 162 may be data (e.g., sensor data 154, metrology data 156, and/or aggregated part-sensor-metrology data 160) for which predictive data 164 is to be generated (e.g., for performing corrective actions based on the historical data).

Part data 152 may include part values and identifiers 158. Sensor data 154 may include sensor values and identifiers 158. Metrology data 156 may include metrology values and identifiers 158. Each instance (e.g., set) of part data 152, sensor data 154, and metrology data 156 may correspond to corresponding substrate processing equipment 134 (e.g., associated with a substrate equipment identifier), a corresponding part of substrate processing equipment 134 (e.g., associated with a part identifier), a corresponding product carrier (e.g., associated with an identifier), a corresponding timestamp (e.g., associated with an identifier), and/or a corresponding product (e.g., associated with a product identifier).

In some embodiments, the client device 106 may store current data 162 (e.g., part, sensor, and/or metrology data received after the generating of the aggregated part-sensor-metrology data 160) in the data store 150 and the predictive server 112 may retrieve the current data 162 from the data store 150. In some embodiments, the predictive server 112 may store output (e.g., predictive data 164) of the trained machine learning model 190 in the data store 150 and the client device 106 may retrieve the output from the data store 150.

In some embodiments, predictive system 110 further includes server machine 170 and server machine 180. Server machine 170 includes a data set generator 172 that is capable of generating data sets (e.g., a set of data inputs, a set of data inputs and a set of target outputs) to train, validate, and/or test a machine learning model 190. Some operations of data set generator 172 are described in detail below with respect to FIGS. 3A and 4A. In some embodiments, the data set generator 172 may partition the aggregated part-sensor-metrology data 160 into a training set (e.g., sixty percent of the aggregated part-sensor-metrology data 160), a validating set (e.g., twenty percent of the aggregated part-sensor-metrology data 160), and a testing set (e.g., twenty percent of the aggregated part-sensor-metrology data 160). In some embodiments, the predictive system 110 (e.g., via predictive component 114) generates multiple sets of features. For example a first set of features may be a first set of data (e.g., from a first set of sensors) that correspond to each of the data sets (e.g., training set, validation set, and testing set) and a second set of features may be a second set of types of data (e.g., from a second set of sensors different from the first set of sensors) that correspond to each of the data sets.

Server machine 180 includes a training engine 182, a validation engine 184, selection engine, and/or a testing engine 186. An engine (e.g., training engine 182, a validation engine 184, selection engine 185, and a testing engine 186) may refer to hardware (e.g., circuitry, dedicated logic, programmable logic, microcode, processing device, etc.), software (such as instructions run on a processing device, a general purpose computer system, or a dedicated machine), firmware, microcode, or a combination thereof. The training engine 182 may be capable of training a machine learning model 190 using one or more sets of features associated with the training set from data set generator 172. The training engine 182 may generate multiple trained machine learning models 190, where each trained machine learning model 190 corresponds to a distinct set of features of the training set (e.g., sensor data from a distinct set of sensors). For example, a first trained machine learning model may have been trained using all features (e.g., X1-X5), a second trained machine learning model may have been trained using a first subset of the features (e.g., X1, X2, X4), and a third trained machine learning model may have been trained using a second subset of the features (e.g., X1, X3, X4, and X5) that may partially overlap the first subset of features.

The validation engine 184 may be capable of validating a trained machine learning model 190 using a corresponding set of features of the validation set from data set generator 172. For example, a first trained machine learning model 190 that was trained using a first set of features of the training set may be validated using the first set of features of the validation set. The validation engine 184 may determine an accuracy of each of the trained machine learning models 190 based on the corresponding sets of features of the validation set. The validation engine 184 may discard trained machine learning models 190 that have an accuracy that does not meet a threshold accuracy. In some embodiments, the selection engine 185 may be capable of selecting one or more trained machine learning models 190 that have an accuracy that meets a threshold accuracy. In some embodiments, the selection engine 185 may be capable of selecting the trained machine learning model 190 that has the highest accuracy of the trained machine learning models 190.

The testing engine 186 may be capable of testing a trained machine learning model 190 using a corresponding set of features of a testing set from data set generator 172. For example, a first trained machine learning model 190 that was trained using a first set of features of the training set may be tested using the first set of features of the testing set. The testing engine 186 may determine a trained machine learning model 190 that has the highest accuracy of all of the trained machine learning models based on the testing sets.

The machine learning model 190 may refer to the model artifact that is created by the training engine 182 using a training set that includes data inputs and, in some embodiments, corresponding target outputs (correct answers for respective training inputs). Patterns in the data sets can be found that cluster the data input and/or map the data input to the target output (the correct answer), and the machine learning model 190 is provided mappings that captures these patterns. The machine learning model 190 may use one or more of linear regression, random forest, neural network (e.g., artificial neural network), etc.

Predictive component 114 may provide current data 162 to the trained machine learning model 190 and may run the trained machine learning model 190 on the input to obtain one or more outputs. The predictive component 114 may be capable of determining (e.g., extracting) predictive data 164 from the output of the trained machine learning model 190 and may determine (e.g., extract) confidence data from the output that indicates a level of confidence that the predictive data 164 corresponds to the part and/or substrate of the substrate processing equipment 134. The predictive component 114 or corrective action component 108 may use the confidence data to decide whether to cause a corrective action associated with the substrate processing equipment 134 based on the predictive data 164.

The confidence data may include or indicate a level of confidence that the predictive data 164 corresponds to the current data 162. In one example, the level of confidence is a real number between 0 and 1 inclusive, where 0 indicates no confidence that the predictive data 164 corresponds to the current data 162 and 1 indicates absolute confidence that the predictive data 164 corresponds to the current data 162. In some embodiments, the system 100 may use predictive system 110 to determine predictive data 164 instead of using the metrology equipment 144 to determine metrology data. In some embodiments, responsive to the confidence data indicating a level of confidence that is below a threshold level, the system 100 may cause the metrology equipment 144 to generate the metrology data. Responsive to the confidence data indicating a level of confidence below a threshold level for a predetermined number of instances (e.g., percentage of instances, frequency of instances, total number of instances, etc.) the predictive component 114 may cause the trained machine learning model 190 to be re-trained (e.g., based on the current data 162 and performance data 166 that corresponds to the current data 162, etc.).

For purpose of illustration, rather than limitation, aspects of the disclosure describe the training of a machine learning model using aggregated part-sensor-metrology data 160 and inputting current data 162 into the trained machine learning model to determine predictive data 164. In other implementations, a heuristic model or rule-based model is used to determine predictive data 164 (e.g., without using a trained machine learning model). Predictive component 114 may monitor aggregated part-sensor-metrology data 160. Any of the information described with respect to data inputs 301 of FIG. 3A may be monitored or otherwise used in the heuristic or rule-based model.

In some embodiments, the functions of data integration server 102, client device 106, predictive server 112, sensor server 132, metrology server 142, server machine 170, and server machine 180 may be provided by a fewer number of machines. For example, in some embodiments server machines 170 and 180 may be integrated into a single machine, while in some other embodiments, server machine 170, server machine 180, and predictive server 112 may be integrated into a single machine. In some embodiments, sensor server 132, metrology server 142, and data integration server 102 may be integrated into a single machine.

In general, functions described in one embodiment as being performed by data integration server 102, client device 106, predictive server 112, sensor server 132, metrology server 142, server machine 170, and server machine 180 can also be performed on predictive server 112 in other embodiments, if appropriate. In addition, the functionality attributed to a particular component can be performed by different or multiple components operating together. For example, in some embodiments, the predictive server 112 may determine the corrective action based on the predictive data. In another example, client device 106 may determine the predictive data 164 based on output from the trained machine learning model.

In addition, the functions of a particular component can be performed by different or multiple components operating together. One or more of the predictive server 112, server machine 170, or server machine 180 may be accessed as a service provided to other systems or devices through appropriate application programming interfaces (API).

In embodiments, a "user" may be represented as a single individual. However, other embodiments of the disclosure encompass a "user" being an entity controlled by a plurality of users and/or an automated source. For example, a set of individual users federated as a group of administrators may be considered a "user."

Although embodiments of the disclosure are discussed in terms of generating aggregated part-sensor-metrology data 160 to perform a corrective action in manufacturing facilities (e.g., substrate manufacturing facilities), embodiments may also be generally applied to aggregating types of data to perform an action. Embodiments may be generally applied to integrating different types of data. For example, sensor data may be aggregated with corresponding component failure data for predicting end of life of components. In another example, images may be aggregated with corresponding image classification for predicting image classification of images.

Figure 2A:
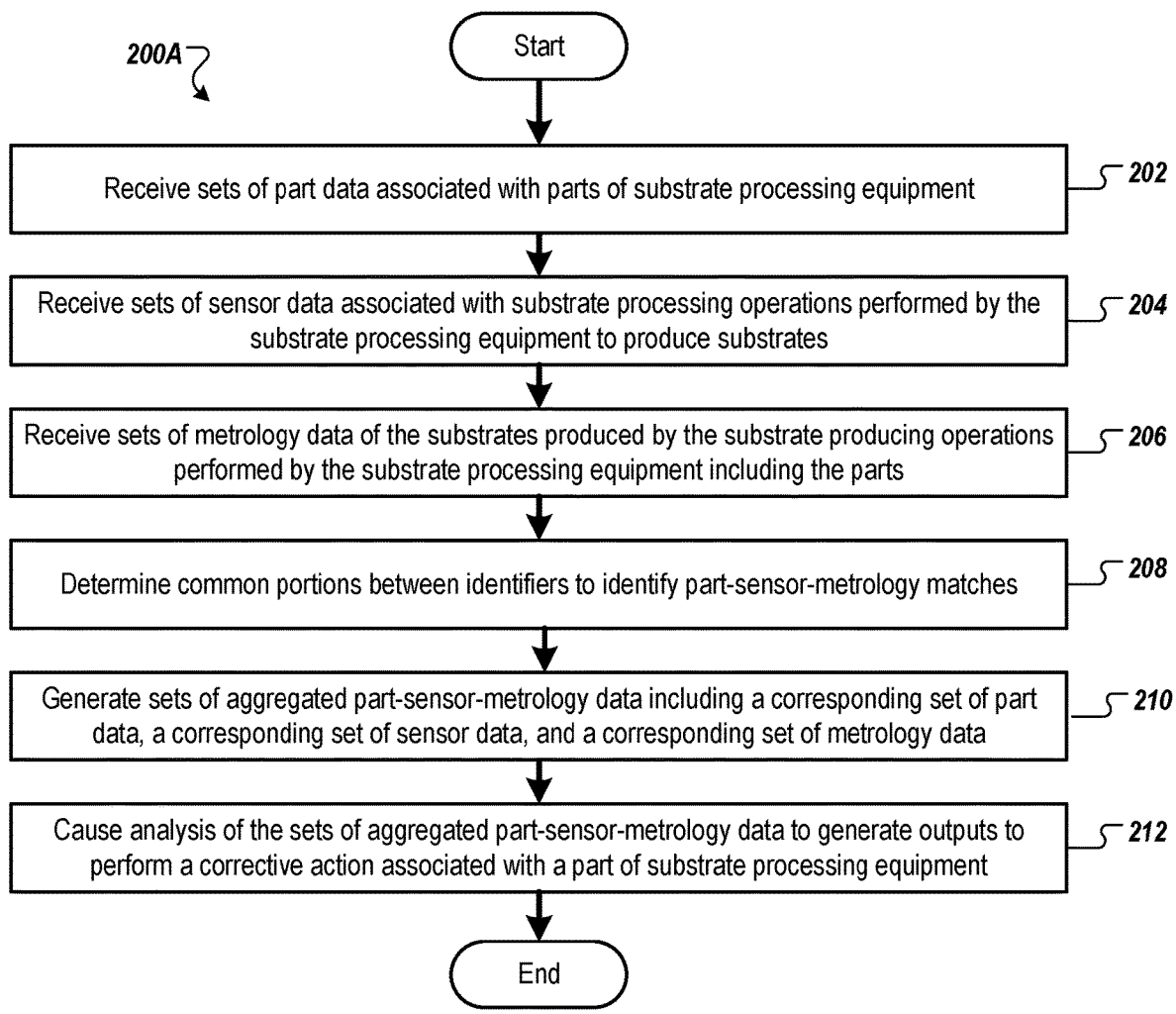
FIG. 2A is a flow diagram of a method of part, sensor, and metrology data integration, according to certain embodiments.

FIG. 2A is a flow diagram of a method 200A of part, sensor, and metrology data integration, according to certain embodiments. Method 200A may be performed by processing logic that may include hardware (e.g., circuitry, dedicated logic, programmable logic, microcode, processing device, etc.), software (such as instructions run on a processing device, a general purpose computer system, or a dedicated machine), firmware, microcode, or a combination thereof. In one embodiment, method 200A may be performed, in part, by data integration server 102 (e.g., data integration component 104). In some embodiments, a non-transitory storage medium stores instructions that when executed by a processing device (e.g., of data integration server 102) cause the processing device to perform method 200A.

For simplicity of explanation, method 200A is depicted and described as a series of acts. However, acts in accordance with this disclosure can occur in various orders and/or concurrently and with other acts not presented and described herein. Furthermore, not all illustrated acts may be performed to implement the method 200A in accordance with the disclosed subject matter. In addition, those skilled in the art will understand and appreciate that the method 200A could alternatively be represented as a series of interrelated states via a state diagram or events.

Referring to FIG. 2A, at block 202 the processing logic receives (e.g., from part server 122, from data store 150) sets of part data associated with parts of substrate processing equipment. A part may be assigned an identifier. In some embodiments, a part is assigned at least two unique identifiers including a part number (e.g., including a revision number) and a serial number. After manufacturing the part, dimensions (e.g., size, weight, surface roughness, location of features, geometry of features, diameter of holes, location of holes, circularity of holes, difference between smallest and largest holes in the part, range of hole diameters in the part, surface topology, durometer, hardness, etc.) may be measured (e.g., via automated optical inspection (AOI), atomic force microscope (AFM), and/or coordinate measurement (CMM)). The part data may include information of where the part was made, how the part was made (e.g., manufacturing processes, machining, grinding, joining, welding, cleaning, brazing, etc.), when the part was made, cure time, environmental conditions (e.g., temperature, humidity, pressure, etc.) of storage and transportation of the part, how long the part was stored, when the part was installed, measurements of the part, one or more identifiers of the part, etc.

The part data may include part measurement data and may be stored under the part number and serial number in a manufacturing database. Responsive to the part being installed into substrate processing equipment (e.g., semiconductor manufacturing system), the part number, serial number, and date (e.g., date of installation) may be recorded into a general database. The general database may copy the part measurement data from the manufacturing database (e.g., using the part number and/or serial number to identify the part measurement data) into the general database.

In some embodiments, the part data includes AOI measurements, such as through hole configuration (e.g., provide light on the backside and measure illumination on the other side, which can be used for hole drilling), blind hole configuration (e.g., light on same side as measurement, which can be used after brazing), backlight illumination (e.g., take image and fit a circle), front light (or ring light) illumination, etc. Focus, contrast, and image analysis can be controlled to optimize results.

The sets of part data my include part manufacturing data (e.g., manufacturing parameters, process parameters, hardware parameters, etc. of the part manufacturing equipment), part measurement data, and/or part material property data. At least a portion of the sets of part data may be measured via one or more of AOI equipment, AFM, and/or a CMM machine). Each of the sets of part data may include part values associated with producing the part and a part identifier.

The part data 152 may include multiple sets of part data, where each set of part data includes part values and one or more identifiers and a timestamp (e.g., a run date, a run hour, etc. corresponding to when the part was processed by the part manufacturing equipment 124).

In some embodiments, for each set of part data 152, the part server 122 may receive part values from sensors 126 (e.g., associated with part manufacturing operations of part manufacturing equipment 124 to produce parts) and may receive an identifier from identifier reader 128.

The identifiers may be added to files of part data 152 as a field or attribute. In some embodiments, the part server 122 stores identifier information on files of part data 152.

At block 204, the processing logic receives (e.g., from sensor server 123, from data store 150) sets of sensor data associated with substrate processing operations performed by the substrate processing equipment to produce substrates. Each of the sets of sensor data may include sensor values associated with producing substrates by the substrate processing equipment and a sensor data identifier.

As substrates are produced by the substrate processing equipment (e.g., substrates run on a semiconductor manufacturing system), sensor data (e.g., pressure, temperature, time, gas flows, etc.) is recorded into a sensor database along with tracking information on the wafer (e.g., FOUP number, slot number, and date).

The sensor data 154 may include multiple sets of sensor data, where each set of sensor data includes sensor values and one or more identifiers (e.g., sensor data identifier such as LOT_ID, sensor carrier identifier such as FOUP ID, product identifier) and a timestamp (e.g., a run date, a run hour, etc. corresponding to when the product was processed by the substrate processing equipment 134).

In some embodiments, for each set of sensor data 154, the sensor server 132 may receive sensor values from sensors 136 (e.g., associated with substrate processing operations of substrate processing equipment 134 to produce substrates) and may receive an identifier (e.g., sensor carrier identifier such as FOUP ID) from identifier reader 138 (e.g., FOUP RFID reader) associated with a substrate carrier (e.g., FOUP) of the substrate. For each set of sensor data, the sensor server 132 may generate an identifier (e.g., LOT_ID) based on the sensor carrier identifier and a timestamp (e.g., by concatenating at least a portion of the sensor carrier identifier and at least a portion of the timestamp). For example, for a sensor carrier identifier of FOUP ID 3044 and a timestamp of Nov. 14, 2018, the sensor server 132 may generate a sensor data identifier of F3044_111418. The joining character could be any character, such as "−," "+," etc. as chosen or convenient for the software architecture.

The identifiers may be added to files of sensor data 154 as a field or attribute. In some embodiments, the sensor server 132 stores carrier identifier (e.g., FOUP ID) information on files of sensor data 154. In some embodiments, the sensor server 132 auto-creates a unique sensor data identifier (e.g., LotID) based on FOUP ID plus date stamp plus timestamp.

At block 206, the processing logic receives (e.g., from metrology server 142, from data store 150) sets of metrology data of the substrates produced by the substrate processing operations performed by the substrate processing equipment including the parts. Each of the sets of metrology data may include metrology values associated with the part produced by the substrate processing equipment and a part identifier.

After the substrates are processed, the substrates are measured on a metrology tool (e.g., metrology equipment) and the substrate measurements (e.g., thickness, film thickness, layer thickness, refractive index, particle numbers, on-wafer metrology data, imaging data, etc.) is recorded in a metrology database along with tracking information on the wafer (e.g., FOUP number, slot number, and date).

The metrology data 156 may include multiple sets of metrology data, where each set of metrology data includes metrology values and identifiers. Each identifier may include a metrology carrier identifier (e.g., FOUP ID), a product identifier, and/or a timestamp (e.g., date, hour, etc. corresponding to when the metrology was measured).

In some embodiments, for each set of metrology data 156, the metrology server 142 may receive metrology values from metrology equipment 144 (e.g., associated with substrates produced by substrate processing operations of substrate processing equipment 134) and may receive an identifier (e.g., a metrology carrier identifier, such as FOUP ID) from identifier reader 146 (e.g., FOUP RFID reader) associated with a product carrier (e.g., FOUP) of the product. For each set of metrology data, the metrology server 142 may generate an identifier 158 based on the metrology carrier identifier and a timestamp. For example, for a metrology carrier identifier of F3044 (e.g., that matches the sensor carrier identifier of the corresponding sensor data 154) and a timestamp of Nov. 14, 2018, the sensor server 132 may generate a metrology data identifier of F3044_111418. The metrology data 156 may be saved in a metrology file that has the metrology data identifier (e.g., LOT_ID) and additional contextual information (e.g., product identifier, etc.).

In some embodiments, the same product carrier (e.g., FOUP) may be associated with the same product in the sensor system 130 (e.g., performing substrate processing of the substrates) and in the metrology system 140 (e.g., measuring the wafers). For the same product, the sensor carrier identifier and the metrology carrier identifier may be the same carrier identifier.

In some embodiments, the metrology server 142 may determine if the metrology data 156 corresponds to a pre-measurement (e.g., metrology data 156 provided before the performing of substrate processing of the substrates during which the sensor data 154 is obtained) or a post-measurement (e.g., metrology data 156 provided after the performing of substrate processing of the substrates during which the sensor data 154 is obtained). The metrology server 142 may include in the identifiers 158 an indication of whether the corresponding metrology data 156 is a pre-measurement or a post-measurement. For example, the file name of metrology data 156 corresponding to pre-measurements may contain "PRE" and file names without "PRE" may be considered post-measurement.

In some embodiments, the sensor data 154 corresponding to a set of products is provided from the sensors 136 to the sensor server 132 at a first point in time and the metrology data 156 corresponding to the same set of products are provided at a second point in time. In some embodiments, the first point in time and the second point in time correspond to the same date (e.g., same date stamp). In some embodiments, the first point in time and the second point in time are the closest points in time for the corresponding carrier identifiers that match (e.g., for the same FOUP ID). In some embodiments, for metrology data 156 that are pre-measurements, the second point in time is the soonest point in time before the first point in time for corresponding carrier identifiers that match (e.g., for the same FOUP ID). In some embodiments, for portions of metrology data 156 that are post-measurements, the second point in time is the soonest point in time after the first point in time for corresponding carrier identifiers that match (e.g., for the same FOUP ID).

In some embodiments, the identifiers 158 (e.g., FOUP ID plus timestamp) are auto-generated by the part server 122, sensor server 132, and/or metrology server 142. In some embodiments, the identifiers 158 are generated by user input. For example, the part server 122, sensor server 132, and/or metrology server 142 may receive a request (e.g., work order) from a user (e.g., process engineer) to access (e.g., view, store, etc.) a set of part data 152, sensor data 154, and/or metrology data 156. The part server 122, sensor server 132, and/or metrology server 142 may transmit the set of metrology data 156 to a centralized database for use by the user. The identifier 158 (e.g., FOUP ID plus timestamp, sequence ID) may be part of a created filename for the part data 152, sensor data 154, and/or metrology data 156. The identifier may be created by concatenating information (e.g., FOUP ###_DateStamp, such as FOUP ID 3044 run on Nov. 14, 2018 having the following string in filename FOUP3044_111418 along with other contextual information). In some embodiments, the processing logic (e.g., via data integration component 104) may use a manually-input identifier 158 instead of an auto-generated identifier 158 (e.g., to verify or spot check the auto-generated identifier).

In some embodiments, at block 208, the processing logic determines common portions between identifiers (e.g., part identifier, sensor data identifier, metrology data identifier) to identify part-sensor-metrology matches. In some embodiments, the common portions are substrings (e.g., FOUP3044_111418) between identifiers 158 of part data 152, sensor data 154, and/or metrology data 156. In some embodiments, the processing logic searches the part server 122, the sensor server 132, and the metrology server 142 and matches common portions (e.g., substrings FOUP3044_111418) on the part server 122, the sensor server 132, and the metrology server 142.

In some embodiments, each common portion (e.g., substring) includes a corresponding carrier identifier that match (e.g., are the same FOUP ID). Each common portion may include a corresponding sensor timestamp (e.g., run date) and a corresponding metrology timestamp that are most proximate of carrier matches (e.g., are the same day, are the closest points in time, etc.).

In some embodiments, the processing logic identifies a pre-measurement set of metrology data 156 and/or a post-measurement set of metrology data that correspond to a set of sensor data 154. To determine pre-measurement metrology data for a run date (e.g., sensor timestamp) corresponding to a set of sensor data 154, the processing logic determines all sets of metrology data 156 (e.g., metrology files from all metrology equipment 144) that have corresponding timestamps a predetermined amount of time before the run date (e.g., look back five days from the run date, common portions for the run date and the previous five days, etc.), that match the carrier identifier (e.g., same FOUP ID), that match the product identifier (e.g., same slot number), and that are pre-measurements (e.g., have "PRE" in the filenames). The processing logic may select the metrology data 156 with a corresponding timestamp closest before the run date as the pre-measurement metrology data to be linked to the sensor data 154.

To determine post-measurement metrology data for the run date, the processing logic determines all sets of metrology data 156 (e.g., metrology files from all metrology equipment 144) that have corresponding timestamps a predetermined amount of time after the run date (e.g., look forward five days from the run date, common portions for the run date and the subsequent five days, etc.), that match the carrier identifier, match the product identifier, and are post-measurements (e.g., do not have "PRE" in the filenames). The processing logic may select the metrology data 156 with a corresponding timestamp closest after the run date as the post-measurement metrology data to be linked to the sensor data 154.

The processing logic may select one or more sets of metrology data 156 (e.g., closest pre-measurement metrology data and closest post-measurement metrology data) to be linked to a set of sensor data 154.

In some embodiments, sensor data 154 is stored by run (e.g., substrate processing operation, manufacturing process). Each set of sensor data 154 may correspond to the same run. The sensor data 154 may include an identifier of corresponding substrate processing equipment 134 (e.g., tool ID), a identifier of the corresponding manufacturing process (e.g., run ID), a timestamp (e.g., manufacturing process start time, run start time, such as 2018-11-14 5:00:00.000), a sensor data identifier (e.g., lot ID, carrier identifier joined with time stamp, such as F3044_111418), and a manufacturing process identifier (e.g., recipe). An example data structure (e.g., table) of sensor data 154 is shown in Table 1.

TABLE 1

| ToolID | RunID | RunStartTime | LotID | Recipe |
|---|---|---|---|---|
| Tool A | Run 1 | 2018 Nov. 14 5:00:00.000 | F3044_111418 | Recipe A |
| Tool A | Run 3 | 2018 Nov. 14 5:10:00.000 | F3044_111418 | Recipe A |
| Tool B | Run 2 | 2018 Nov. 14 5:00:00.000 | F3044_111418 | Recipe A |
| Tool B | Run 4 | 2018 Nov. 14 5:10:00.000 | F3044_111418 | Recipe A |
| Tool B | Run 5 | 2018 Nov. 14 5:20:00.000 | F3044_111418 | Recipe A |

In some embodiments, metrology data 156 is stored in a file that includes a file identifier (e.g., file ID), file name, and a metrology process (e.g., dielectric measurement, ellipsometry, etc.). The file name may include the carrier identifier (e.g., F3044), a timestamp (e.g., 111418) or time range (e.g., 111418-11.15.18), and a product identifier (e.g., indicating a slot number such as "_s1"). An example data structure (e.g., table) of metrology data is shown in Table 2.

TABLE 2

| FileID | FileName | Metrology |
|---|---|---|
| File 1 | Data-F3044_111418-11.15.18-Data_s1.csv | Ellipsometry |
| File 2 | Data-F3044_111418-11.15.18-Data_s2.csv | Ellipsometry |
| File 3 | Data-F3044_111418-11.15.18-Data_s3.csv | Ellipsometry |
| File 4 | Data-F3044_111418-11.15.18-Data_s4.csv | Ellipsometry |
| File 5 | Data-F3044_111418-11.15.18-Data_s5.csv | Ellipsometry |

The processing logic may receive the sensor data 154 from the sensor server 132 and the metrology data 156 (e.g., metrology file data) from the metrology server 142 (e.g., shared folders). The processing logic may identify the common attributes (e.g., carrier identifier, timestamp, portions, substrings, etc.) between the sensor data 154 and the metrology data 156. Because of slot integrity (e.g., products in same order in manufacturing processes and metrology processes), the processing logic may be able to identify the sensor data 154 that corresponds to the product identifiers 156 of the metrology data 156 by the order of the sensor data 154 (e.g., first timestamp of sensor data 154 corresponds to the first product identifier). The processing logic may provide a linking between the metrology data 156 (e.g., metrology file) and sensor data 154 (e.g., run data) by associating file identifiers, identifiers of manufacturing equipment, and manufacturing process identifiers. The processing logic may provide a GUI to display the linking information. An example data structure (e.g., table) of the linking between the sensor data 154 and the metrology data 156 is shown in Table 3.

TABLE 3

| FileID | ToolID | RunID |
|---|---|---|
| File 2 | Tool A | Run 1 |
| File 4 | Tool A | Run 3 |
| File 1 | Tool B | Run 2 |
| File 3 | Tool B | Run 4 |
| File 5 | Tool B | Run 5 |

Table 3 shows that the product in slot 2 was processed at 5:00 by tool A, the product in slot 4 was processed at 5:10 by tool A, the product in slot 1 was processed at 5:00 by tool B, the product in slot 3 was processed at 5:10 by tool B, and the product in slot 5 was processed at 5:20 by tool B. The processing logic may generate aggregated part-sensor-metrology data 160 that includes sensor data 154, metrology data 156, and an indication of common attributes (e.g., similar to or different from the linking attributes in Table 3).

At block 210, the processing logic generates sets of aggregated part-sensor-metrology data (e.g., aggregated part-sensor-metrology data structure or data table) including a corresponding set of part data, a corresponding set of sensor data, and a corresponding set of metrology data. The processing logic may generate a set of aggregated part-sensor-metrology data for each of the part-sensor-metrology matches.

In some embodiments, sensor data associated with production of a substrate from the sensor database and metrology data of the substrate from the metrology database are linked by matching tracking information (e.g., FOUP number, slot number, and date). Sensor-metrology data may be linked with the part data from the manufacturing database by using a date (e.g., date of installation of the part, date of manufacture of the part, date of the substrate processing operation). The linked data can be output in a format (e.g., aggregated part-sensor-metrology data) that can be used for manual data processing (e.g., manual computing, manual processing, using a spreadsheet or data analysis software) or automated data processing (e.g., automated computing, automated processing, automated machine learning models).

Each set of aggregated part-sensor-metrology data may include a respective set of part data, a respective set of sensor data, and a respective set of metrology data that each correspond to a common identifier 158 (e.g., that are integrated, that are aggregated, that are linked, etc.). For example, an aggregated part-sensor-metrology data structure may include part data, sensor data (e.g., sensor_1 to sensor N), product identifier (e.g., wafer_ID), carrier identifier (e.g., FOUP_ID), sensor timestamp (e.g., datestamp, metrology data (e.g., thickness, refractive index (RI), dielectric constant (k), etc.), and/or metrology timestamp (e.g., datestamp), where the product identifier 148 and product identifier match, the sensor carrier identifier and the metrology carrier identifier match, and the sensor timestamp and metrology timestamp match.

In some embodiments, the processing logic joins or links files with a product identifier (e.g., Wafer_ID) as a common field or attribute.

At block 212, the processing logic causes analysis of the sets of aggregated part-sensor metrology data to generate outputs to perform a corrective action associated with a part of substrate processing equipment.

Figure 4A:
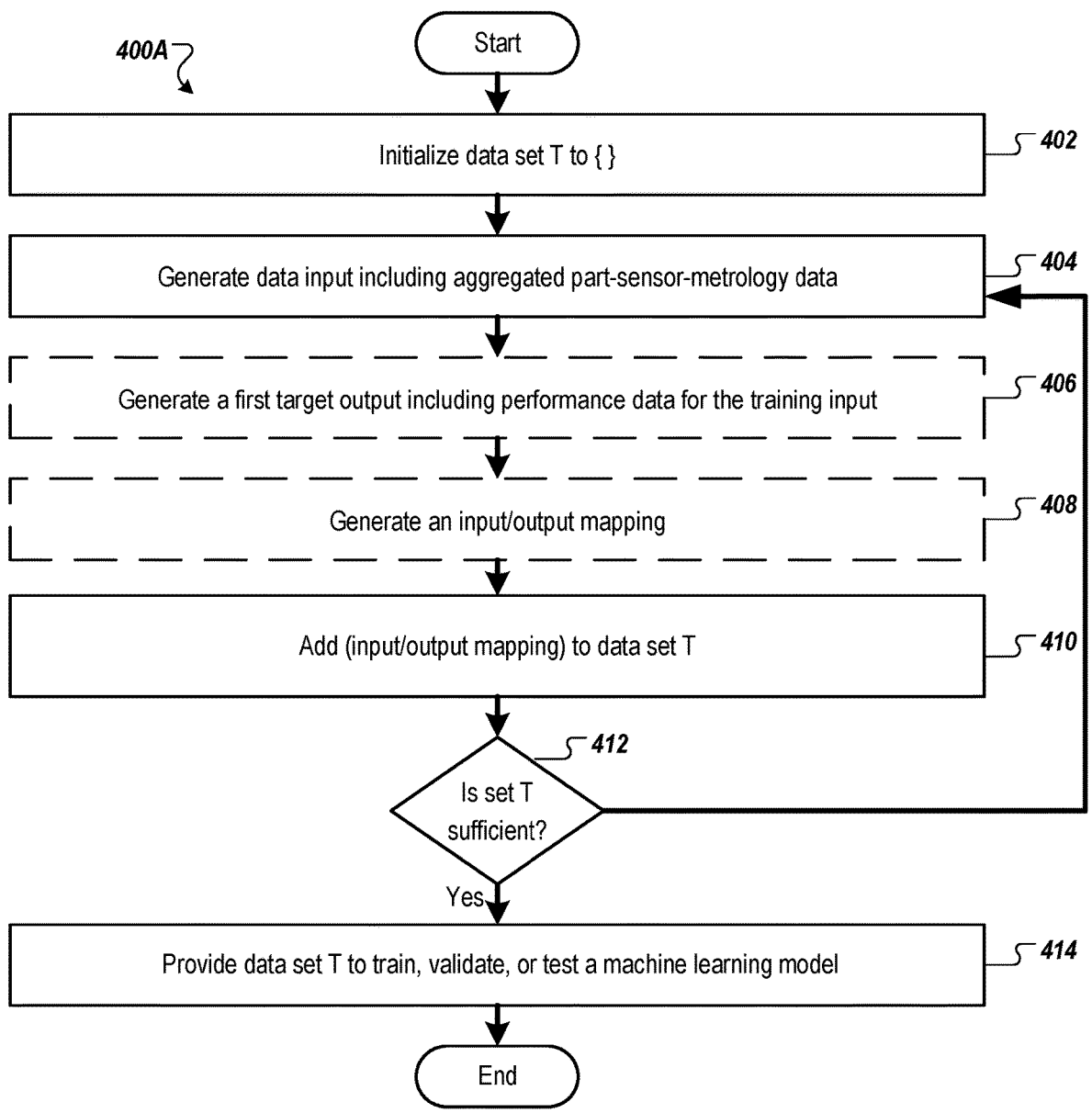
FIGS. 4A-C are flow diagrams of methods associated with part, sensor, and metrology data integration, according to certain embodiments.
Figure 4B:
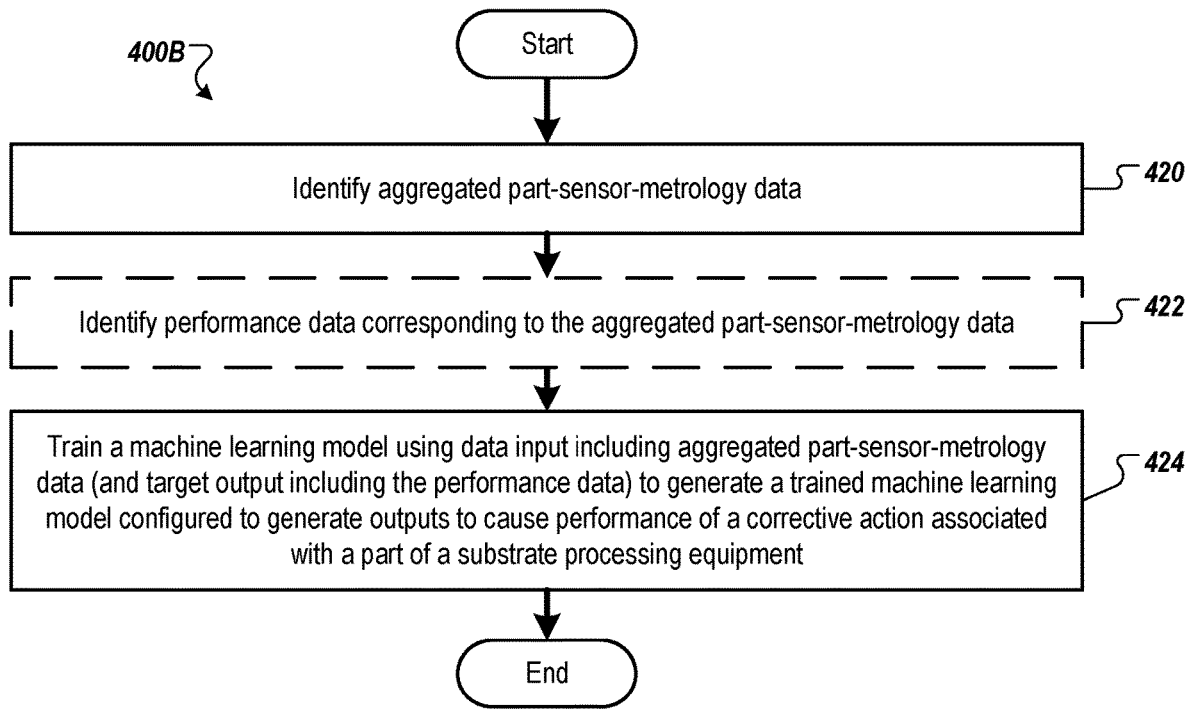

The causing of the analysis of the sets of aggregated part-sensor-metrology data may include providing the sets of aggregated part-sensor-metrology data to train a machine learning model (e.g., see FIG. 4B).

Figure 4C:
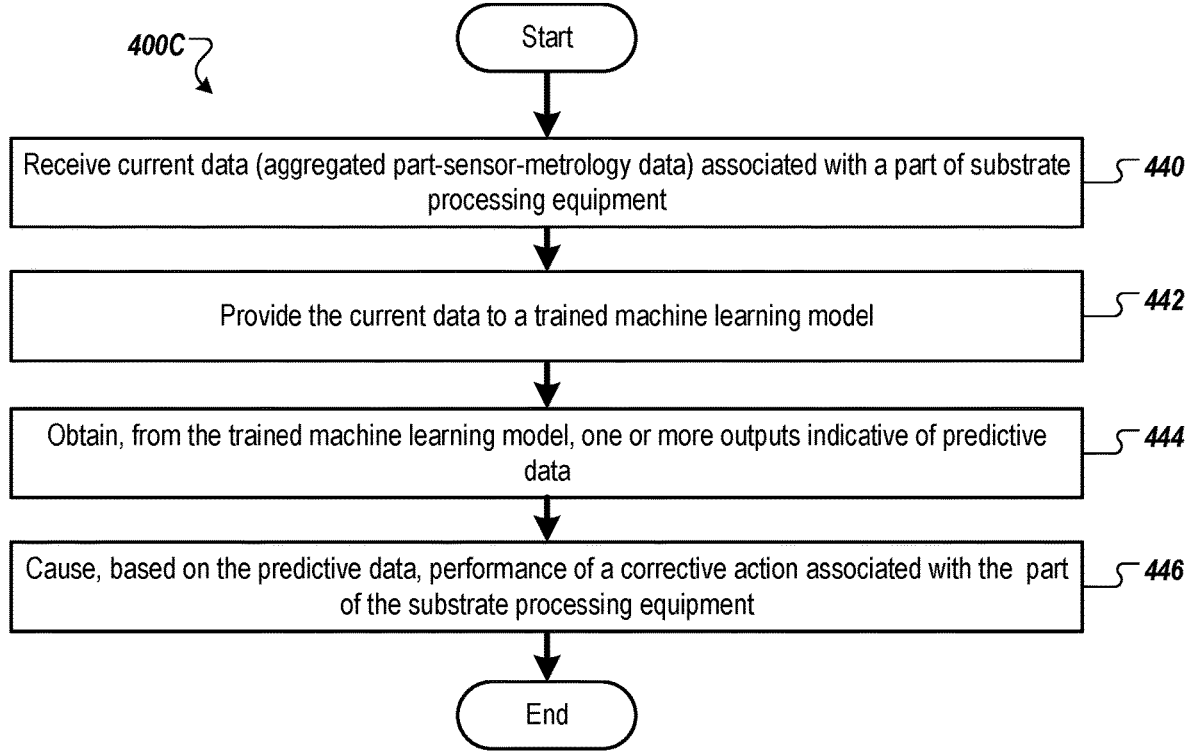

The causing of the analysis of the sets of aggregated part-sensor-metrology data may include providing the sets of aggregated part-sensor-metrology data to a trained machine learning model and receiving, from the trained machine learning model, the one or more outputs (e.g., see FIG. 4C).

The causing of the analysis of the sets of aggregated part-sensor-metrology data may include performing data mining on, determining correlations between (e.g., wafer range and AOI range), root cause amplification of, clustering of, etc. the sets of aggregated part-sensor-metrology data (e.g., to perform root cause analysis). In some embodiments, the causing of the analysis of the sets of aggregated part-sensor-metrology data identifies a general area where the problem lies (e.g., poor uniformity) for performance of further analysis (e.g., determine how to improve uniformity). In some embodiments, the causing of the analysis of the sets of aggregated part-sensor-metrology data includes stages of one or more of clustering, anomaly detection, correlation analysis, etc. For example, the analysis may be used to determine which component is causing the problem, subsequently to determine a feature of the component that is causing the problem, and subsequently to determine a manufacturing parameter that is causing the problem.

The causing of the analysis of the sets of aggregated part-sensor-metrology data may include storing the sets of aggregated part-sensor-metrology data (e.g., to train a machine learning model to provide a trained machine learning model capable of generating the outputs to perform the corrective action). In some embodiments, the processing logic stores the sets of aggregated part-sensor-metrology data in a data store, in a database warehouse, in a technical data warehouse, etc. Each of the sets of aggregated part-sensor-metrology data may be stored in a corresponding data structure (e.g., in a corresponding table, in a corresponding file, etc.).

In some embodiments, the aggregated part-sensor-metrology data is stored in a database that is to be searched based on part data, sensor data, and/or metrology data to determine optimal part design, part manufacturing parameters, part feature layout, part dimensions, part material properties, etc.

In some embodiments, the aggregated part-sensor-metrology data (e.g., unlabeled data) is stored to train a machine learning model (e.g., unsupervised machine learning, clustering, etc.) to generate a trained machine learning model. The trained machine learning model may be capable of generating one or more outputs (e.g., predictive data, an indication to which cluster new data belongs).

In some embodiments, the aggregated part-sensor-metrology data (e.g., labeled data) is stored to train a machine learning model 190 (e.g., supervised machine learning) to generate a trained machine learning model. The trained machine learning model may be capable of generating one or more outputs (e.g., artificial intelligence (AI) applications, such as generating predictive data 164 based on input of current data 162) for performing a corrective action associated with the substrate processing equipment 134.

In some embodiments, the aggregated part-sensor-metrology data is stored in as catalogued data in a centralized location (e.g., data store 150) for future use. Conventionally, part data, sensor data, and metrology data are stored in different locations (e.g., different facilities, on a user's laptop, etc.). There may be hundreds of sensors (e.g., over 500), so part data and sensor data over time take up a lot of storage capacity (e.g., on a user's laptop) and may eventually be discarded. Method 200A may be used to generate and store aggregated part-sensor-metrology data 160 over long periods of time (e.g., months, years) to be used for later analysis for performing corrective actions.

In some embodiments, the processing logic generates the sets of aggregated part-sensor-metrology data without user input of manually associating the part data, sensor data, and metrology data. In some embodiments, the processing logic generates the sets of aggregated part-sensor-metrology data without using an optical character recognition (OCR) system.

In some embodiments, each product carrier has multiple slots that carry a product (e.g., substrate) and slot integrity (e.g., order of the product in the slots) may be maintained when the products are processed by the substrate processing equipment 134 (e.g., on chambers) and are sent for metrology measurements by the metrology equipment 144 (e.g., the first product to be processed by the substrate processing equipment 134 is the first product to be measured by the metrology equipment 144).

In some embodiments, the corrective action includes updating design of a part (e.g., eliminating part manufacturing operations), quality of the part (e.g., reducing part variation, such as improving diameter, location, and/or circularity of holes), dimensions of the part (e.g., updating thickness and/or diameter of a portion of the part), feature layout of the part (e.g., updating hole locations on a part), part manufacturing operations to produce the part (e.g., replacing or avoiding certain manufacturing operations), etc. In some embodiments, the corrective action includes performing root cause analysis to determine updates in the part or to substrate processing operations. In some embodiments, the corrective action includes causing a GUI to display an alert, interrupting operation of the part manufacturing equipment or substrate processing equipment (e.g., stopping the substrate processing equipment 134, stopping a portion of the substrate processing equipment 134, not performing a manufacturing process, etc.), and/or causing updates to manufacturing parameters of the part manufacturing equipment or substrate processing equipment. In some embodiments, the corrective action includes updating substrate processing operations (e.g., adjusting operating conditions to achieve a substrate output).

In some embodiments, method 200A is used to determine differences between similar substrate processing equipment that result in different performance (e.g., differences in parts, differences in manufacturing parameters, etc.).

As a result of the corrective action, new parts may have better quality (e.g., reduced variation, reduced hole size variation, etc.) and/or substrates may have better quality (e.g., have measurements within threshold values).

Figure 2B:
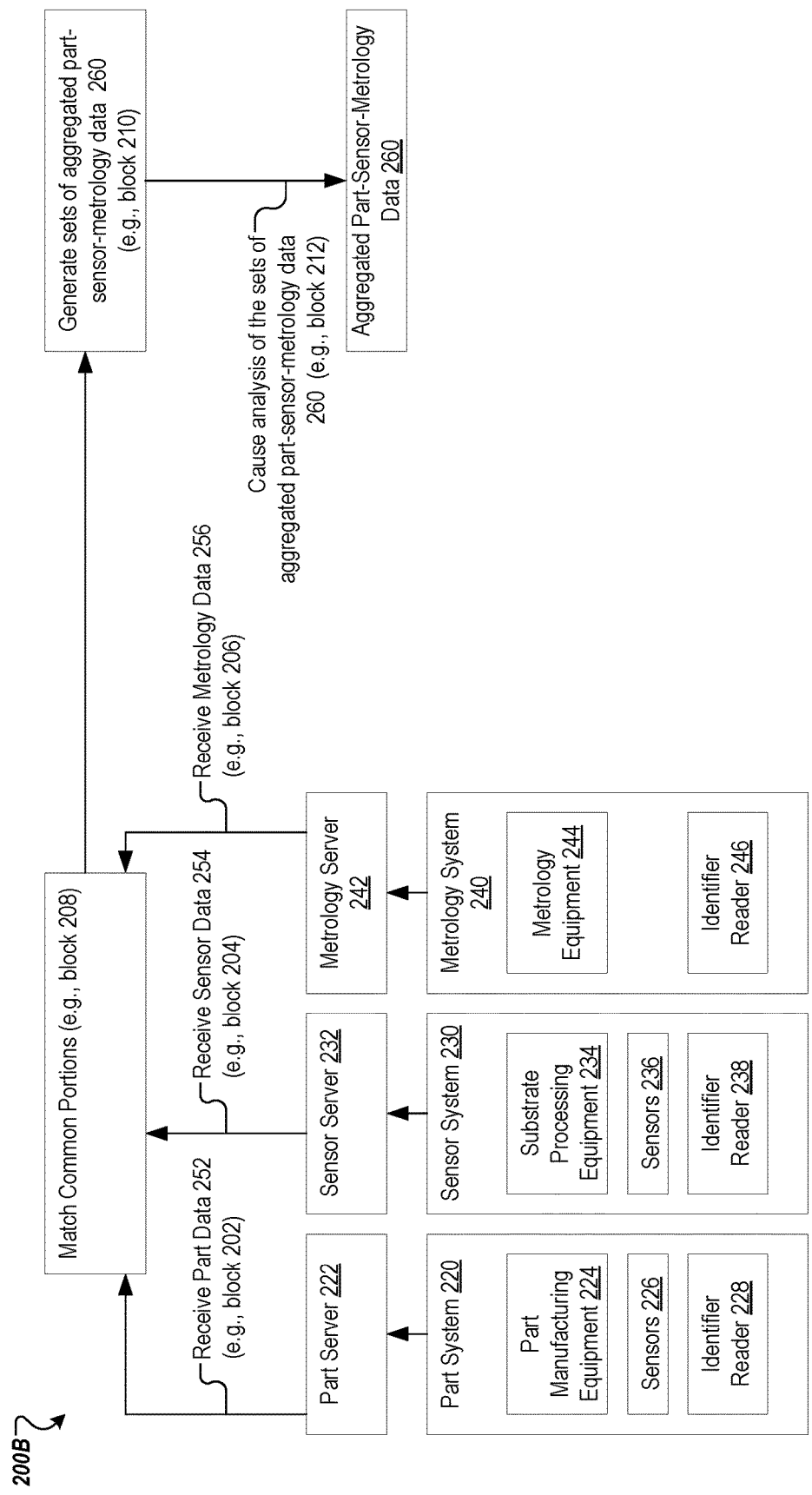
FIG. 2B is a block diagram of part, sensor, and metrology data integration, according to certain embodiments.

FIG. 2B is a block diagram 200B of part, sensor, and metrology data integration, according to certain embodiments. Portions of block diagram 200B may be the similar or the same as blocks of method 200A of FIG. 2A.

Block diagram 200B may include part server 222, part system 220, sensor server 232 (e.g., FSS, sensor server 132 of FIG. 1), sensor system 230 (e.g., tool/process system, sensor system 130 of FIG. 1), metrology server 242, and metrology system 240 (e.g., metrology system 140 of FIG. 1). The part system 220 may include part manufacturing equipment 224, sensors 226 (e.g., sensors 126 of FIG. 1), and an identifier reader 228. The sensor system 230 may include substrate processing equipment 234 (e.g., substrate processing equipment 134 of FIG. 1), sensors 236 (e.g., sensors 136 of FIG. 1), and an identifier reader 238 (e.g., a FOUP RFID reader, identifier reader 138 of FIG. 1). Metrology system 240 may include metrology equipment 244 (e.g., metrology equipment 144 of FIG. 1) and an identifier reader 246 (e.g., FOUP RFID reader, identifier reader 146 of FIG. 1).

The part server 222 may receive part values and part identifiers from part system 220 to generate part data 252 (part data 152 of FIG. 1). The sensor server 232 may receive sensor values and sensor data identifiers from sensor system 230 to generate sensor data 254 (sensor data 154 of FIG. 1). The metrology server 242 may receive metrology values and metrology data identifiers from metrology system 240 to generate sensor data 254 (sensor data 154 of FIG. 1).

The data integration server 102 (e.g., via data integration component 104) may receive the part data 252 (e.g., see block 202), receive the sensor data 254 (e.g., see block 204), and receive the metrology data 256 (e.g., see block 206). In some embodiments, the data integration server 102 may receive user input (e.g., that was manually input) of a FOUP ID and DateStamp from a user data store. The user input may include manual entry of identifiers (e.g., metrology data identifiers). The data integration server 102 may compare the metrology data received from metrology server 242 with the user input to verify accuracy (e.g., spot check) the metrology data 256.

The data integration server 102 may match common portions (e.g., substrings FOUP ####_DateStamp) (e.g., see block 208). The data integration server 102 may generate sets of aggregated part-sensor-metrology data (e.g., see block 210) (e.g., link/join files in a data structure such as a data table) based on the common portions. The data integration server 102 may store the aggregated part-sensor-metrology data 260 (e.g., aggregated part-sensor-metrology data 160 of FIG. 1) in a data store (e.g., data store 150 of FIG. 1, a technical data warehouse (TDW), etc.).

Figure 3A:
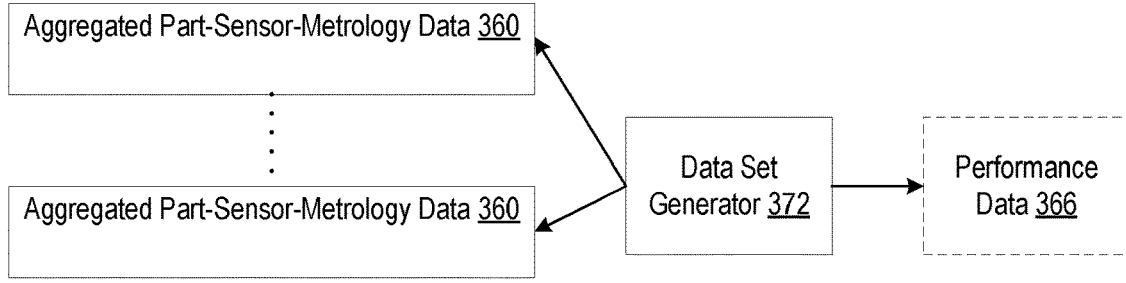
FIG. 3A is an example data set generator to create data sets for a machine learning model, according to certain embodiments.

FIG. 3A is an example data set generator 372 (e.g., data set generator 172 of FIG. 1) to create data sets for a machine learning model (e.g., model 190 of FIG. 1) using aggregated part-sensor-metrology data 360 (e.g., aggregated part-sensor-metrology data 360 of FIG. 1), according to certain embodiments. System 300A of FIG. 3A shows data set generator 372, data inputs 301, and target output 303.

In some embodiments, data set generator 372 generates a data set (e.g., training set, validating set, testing set) that includes one or more data inputs 301 (e.g., training input, validating input, testing input). In some embodiments, the data set further includes one or more target outputs 303 that correspond to the data inputs 301. The data set may also include mapping data that maps the data inputs 301 to the target outputs 303. Data inputs 301 may also be referred to as "features," "attributes," or information." In some embodiments, data set generator 372 may provide the data set to the training engine 182, validating engine 184, or testing engine 186, where the data set is used to train, validate, or test the machine learning model 190. Some embodiments of generating a training set may further be described with respect to FIG. 4A.

In some embodiments, data set generator 372 generates the data input 301 based on aggregated part-sensor-metrology data 360. In some embodiments, the data set generator 372 generates the target output 303 based performance data 366 associated with the aggregated part-sensor-metrology data 360. The data set generator 372 may determine the mapping from each set of the aggregated part-sensor-metrology data 360 to performance data 366.

In some embodiments, data inputs 301 may include one or more sets of features for the aggregated part-sensor-metrology data 360. Each instance of aggregated part-sensor-metrology data 360 may include part data for one or more types of parts, sensor data from one or more types of sensors, and/or metrology data associated with one or more types of substrates.

In some embodiments, data set generator 272 may generate a first data input corresponding to a first set of features to train, validate, or test a first machine learning model and the data set generator 272 may generate a second data input corresponding to a second set of features to train, validate, or test a second machine learning model.

In some embodiments, the data set generator 272 may discretize one or more of the data input 301 or the target output 303 (e.g., to use in classification algorithms for regression problems). Discretization of the data input 301 or target output 303 may transform continuous values of variables into discrete values. In some embodiments, the discrete values for the data input 301 indicate discrete manufacturing parameters to obtain a target output 303 (e.g., discrete property data).

Data inputs 301 and target outputs 303 to train, validate, or test a machine learning model may include information for a particular facility (e.g., for a particular part manufacturing facility or substrate manufacturing facility). For example, the aggregated part-sensor-metrology data 360 and performance data 366 may be for the same manufacturing facility.

In some embodiments, the information used to train the machine learning model may be from specific types of manufacturing equipment (e.g., part manufacturing equipment 124, substrate processing equipment 134) of the manufacturing facility having specific characteristics and allow the trained machine learning model to determine outcomes for a specific group of manufacturing equipment based on input for aggregated part-sensor-metrology data 360 associated with one or more components sharing characteristics of the specific group. In some embodiments, the information used to train the machine learning model may be for components from two or more manufacturing facilities and may allow the trained machine learning model to determine outcomes for components based on input from one manufacturing facility.

In some embodiments, subsequent to generating a data set and training, validating, or testing machine learning model 190 using the data set, the machine learning model 190 may be further trained, validated, or tested (e.g., further aggregated part-sensor-metrology data 160 and performance data 166 of FIG. 1) or adjusted (e.g., adjusting weights associated with input data of the machine learning model 190, such as connection weights in a neural network).

Figure 3B:
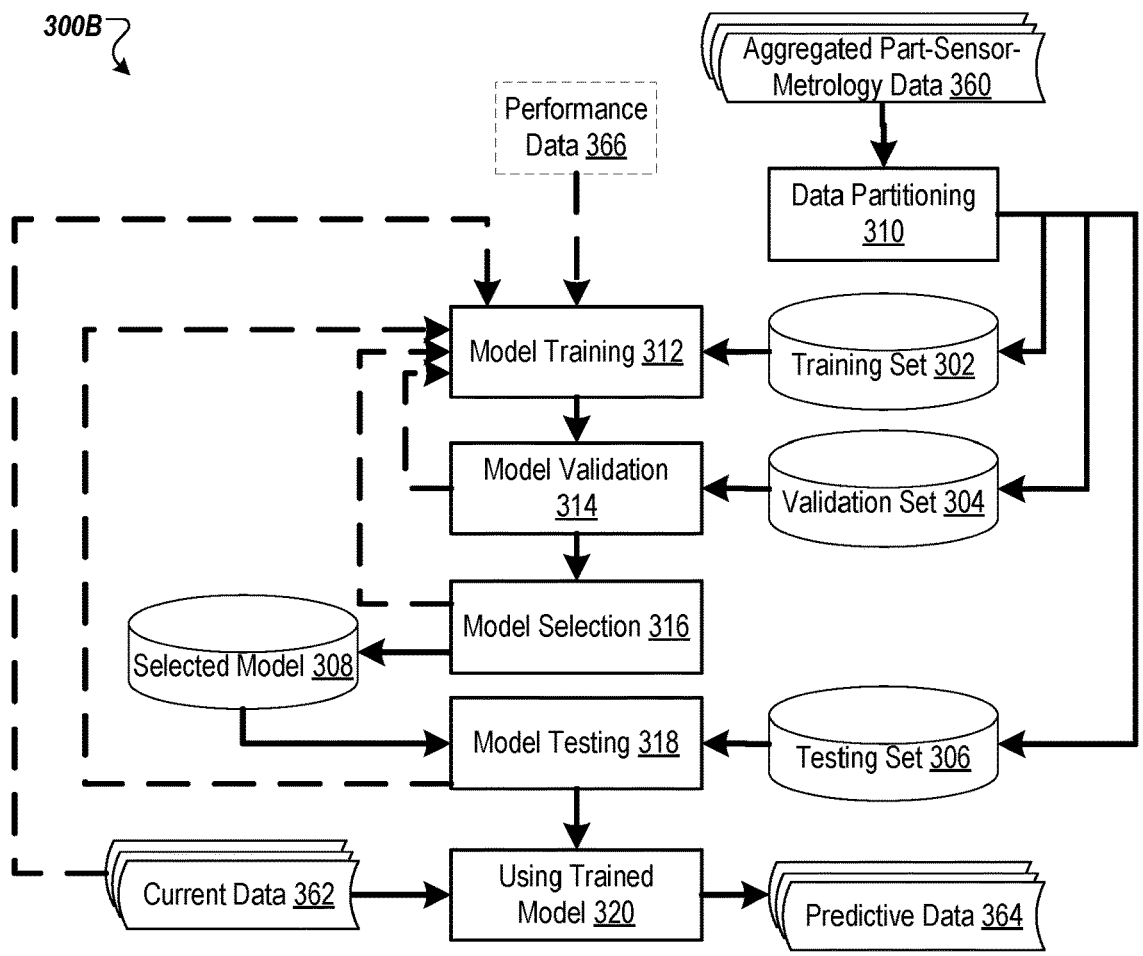
FIG. 3B is a block diagram illustrating determining predictive data, according to certain embodiments.

FIG. 3B is a block diagram illustrating a system 300 for generating predictive data 364 (e.g., predictive data 164 of FIG. 1), according to certain embodiments. The system 300B may be used to determine a corrective action associated with a part of substrate processing equipment 134 based on aggregated part-sensor-metrology data 360 (e.g., aggregated part-sensor-metrology data 360 of FIG. 1).

At block 310, the system 300 (e.g., predictive system 110 of FIG. 1) performs data partitioning (e.g., via data set generator 172 of server machine 170 of FIG. 1) of the aggregated part-sensor-metrology data 360 (e.g., aggregated part-sensor-metrology data 160 of FIG. 1) (and in some embodiments performance data 366) to generate the training set 302, validation set 304, and testing set 306. For example, the training set may be 60% of the aggregated part-sensor-metrology data 360, the validation set may be 20% of the aggregated part-sensor-metrology data 360, and the validation set may be 20% of the aggregated part-sensor-metrology data 360. The system 300 may generate a plurality of sets of features for each of the training set, the validation set, and the testing set. For example, if the aggregated part-sensor-metrology data 360 is associated with 20 sensors (e.g., sensors 126 of FIG. 1) and 100 products (e.g., wafers that each correspond to the sensor data from the 20 sensors), a first set of features may be sensors 1-10, a second set of features may be sensors 11-20, the training set may be products 1-60, the validation set may be products 61-80, and the testing set may be products 81-100. In this example, the first set of features of the training set would be from sensors 1-10 for products 1-60.

At block 312, the system 300 performs model training (e.g., via training engine 182 of FIG. 1) using the training set 302. The system 300 may train multiple models using multiple sets of features of the training set 302 (e.g., a first set of features of the training set 302, a second set of features of the training set 302, etc.). For example, system 300 may train a machine learning model to generate a first trained machine learning model using the first set of features in the training set (e.g., sensor data from sensors 1-10 for products 1-60) and to generate a second trained machine learning model using the second set of features in the training set (e.g., sensor data from sensors 11-20 for products 1-60). In some embodiments, the first trained machine learning model and the second trained machine learning model may be combined to generate a third trained machine learning model (e.g., which may be a better predictor than the first or the second trained machine learning model on its own). In some embodiments, sets of features used in comparing models may overlap (e.g., first set of features being from sensors 1-15 and second set of features being from sensors 5-20). In some embodiments, hundreds of models may be generated including models with various permutations of features and combinations of models.

At block 314, the system 300 performs model validation (e.g., via validation engine 184 of FIG. 1) using the validation set 304. The system 300 may validate each of the trained models using a corresponding set of features of the validation set 304. For example, system 300 may validate the first trained machine learning model using the first set of features in the validation set (e.g., sensor data from sensors 1-10 for products 61-80) and the second trained machine learning model using the second set of features in the validation set (e.g., sensor data from sensors 11-20 for products 61-80). In some embodiments, the system 300 may validate hundreds of models (e.g., models with various permutations of features, combinations of models, etc.) generated at block 312. At block 314, the system 300 may determine an accuracy of each of the one or more trained models (e.g., via model validation) and may determine whether one or more of the trained models has an accuracy that meets a threshold accuracy. Responsive to determining that none of the trained models has an accuracy that meets a threshold accuracy, flow returns to block 312 where the system 300 performs model training using different sets of features of the training set. Responsive to determining that one or more of the trained models has an accuracy that meets a threshold accuracy, flow continues to block 316. The system 300 may discard the trained machine learning models that have an accuracy that is below the threshold accuracy (e.g., based on the validation set).

At block 316, the system 300 performs model selection (e.g., via selection engine 185 of FIG. 1) to determine which of the one or more trained models that meet the threshold accuracy has the highest accuracy (e.g., the selected model 308, based on the validating of block 314). Responsive to determining that two or more of the trained models that meet the threshold accuracy have the same accuracy, flow may return to block 312 where the system 300 performs model training using further refined training sets corresponding to further refined sets of features for determining a trained model that has the highest accuracy.

At block 318, the system 300 performs model testing (e.g., via testing engine 186 of FIG. 1) using the testing set 306 to test the selected model 308. The system 300 may test, using the first set of features in the testing set (e.g., sensor data from sensors 1-10 for products 81-100), the first trained machine learning model to determine the first trained machine learning model meets a threshold accuracy (e.g., based on the first set of features of the testing set 306). Responsive to accuracy of the selected model 308 not meeting the threshold accuracy (e.g., the selected model 308 is overly fit to the training set 302 and/or validation set 304 and is not applicable to other data sets such as the testing set 306), flow continues to block 312 where the system 300 performs model training (e.g., retraining) using different training sets corresponding to different sets of features (e.g., sensor data from different sensors). Responsive to determining that the selected model 308 has an accuracy that meets a threshold accuracy based on the testing set 306, flow continues to block 320. In at least block 312, the model may learn patterns in the aggregated part-sensor-metrology data 360 to make predictions and in block 318, the system 300 may apply the model on the remaining data (e.g., testing set 306) to test the predictions.

At block 320, system 300 uses the trained model (e.g., selected model 308) to receive current data 362 (e.g., current data 162 of FIG. 1, current aggregated part-sensor-metrology data 160 of FIG. 1) and determines (e.g., extracts), from the output of the trained model, predictive data 364 (e.g., predictive data 164 of FIG. 1) to perform corrective actions associated with a part of part manufacturing equipment 124.

In some embodiments, performance data 366 corresponding to the current data 362 is received and the model 308 is re-trained based on the current data 362 and the performance data 366.

In some embodiments, one or more operations of the blocks 310-320 may occur in various orders and/or with other operations not presented and described herein. In some embodiments, one or more operations of blocks 310-320 may not be performed. For example, in some embodiments, one or more of data partitioning of block 310, model validation of block 314, model selection of block 316, or model testing of block 318 may not be performed.

FIGS. 4A-C are flow diagrams of methods 400A-C associated with part, sensor, and metrology data integration, according to certain embodiments. Methods 400A-C may be performed by processing logic that may include hardware (e.g., circuitry, dedicated logic, programmable logic, microcode, processing device, etc.), software (such as instructions run on a processing device, a general purpose computer system, or a dedicated machine), firmware, microcode, or a combination thereof. In some embodiments, method 400A may be performed, in part, by predictive system 110 (e.g., server machine 170, data set generator 172, etc.). Predictive system 110 may use method 400A to at least one of train, validate, or test a machine learning model, in accordance with embodiments of the disclosure. In some embodiments, one or more operations of method 400A may be performed by data set generator 172 of server machine 170 as described with respect to FIGS. 1 and 3A. In some embodiments, methods 400B-C may be performed, in part, by predictive system 110 (e.g., predictive server 112, predictive component 114, etc.). Predictive system 110 may use method 400B to train a machine learning model, in accordance with embodiments of the disclosure. Predictive system 110 may use method 400C to use a trained machine learning model, in accordance with embodiments of the disclosure. In some embodiments, one or more operations of methods 400B-C may be performed by predictive component 114 of predictive server 112 as described with respect to FIGS. 1 and 3B. It may be noted that components described with respect to one or more of FIG. 1, 2, or 3A-B may be used to illustrate aspects of FIGS. 4A-C. In some embodiments, a non-transitory storage medium stores instructions that when executed by a processing device (e.g., of predictive system 110) cause the processing device to perform methods 400A-C.

For simplicity of explanation, methods 400A-C are depicted and described as a series of acts. However, acts in accordance with this disclosure can occur in various orders and/or concurrently and with other acts not presented and described herein. Furthermore, not all illustrated acts may be performed to implement the methods 400A-C in accordance with the disclosed subject matter. In addition, those skilled in the art will understand and appreciate that the methods 400A-C could alternatively be represented as a series of interrelated states via a state diagram or events.

Referring to FIG. 4A, method 400A is associated with generating a data set for a machine learning model for performing a corrective action associated with a part of substrate processing equipment.

At block 402 the processing logic implementing method 400A initializes a training set T to an empty set.

At block 404, processing logic generates first data input (e.g., first training input, first validating input) that includes aggregated part-sensor-metrology data (e.g., aggregated part-sensor-metrology data 160 of FIG. 1). In some embodiments, the first data input may include a first set of features for types of aggregated part-sensor-metrology data and a second data input may include a second set of features for types of aggregated part-sensor-metrology data (e.g., as described with respect to FIG. 3A). The processing logic may generate the data input based on portions of the aggregated part-sensor-metrology data 160 (e.g., extracting part data 152, sensor data 154, and/or metrology data 156 from a data structure or table of aggregated part-sensor-metrology data 160).

In some embodiments, at block 406, processing logic generates a first target output for one or more of the data inputs (e.g., first data input). The first target output may be corresponding performance data (e.g., performance data 366, a label of substrates associated with the aggregated part-sensor-metrology data 160). The processing logic may generate the target output based on the aggregated part-sensor-metrology data 160 (e.g., extracting the part data 152, sensor data 154, and/or metrology data 156 from the same data structure or table of aggregated part-sensor-metrology data 160 from which the sensor data of the data input was extracted).

At block 408, processing logic optionally generates mapping data that is indicative of an input/output mapping. The input/output mapping (or mapping data) may refer to the data input (e.g., one or more of the data inputs described herein), the target output for the data input (e.g., where the target output identifies performance data 166), and an association between the data input(s) and the target output. The mapping data may be based on the common data structure or table of aggregated part-sensor-metrology data 160 from which the data input and the target output were extracted.

At block 410, processing logic adds the data input generated at block 404 and/or the mapping data generated at block 408 to data set T.

At block 412, processing logic branches based on whether data set T is sufficient for at least one of training, validating, and/or testing machine learning model 190. If so, execution proceeds to block 414, otherwise, execution continues back at block 404. In some embodiments, the sufficiency of data set T may be determined based simply on the number of input/output mappings in the data set, while in some other implementations, the sufficiency of data set T may be determined based on one or more other criteria (e.g., a measure of diversity of the data examples, accuracy, etc.) in addition to, or instead of, the number of input/output mappings.

At block 414, processing logic provides data set T (e.g., to server machine 180) to train, validate, and/or test machine learning model 190. In some embodiments, data set T is a training set and is provided to training engine 182 of server machine 180 to perform the training. In some embodiments, data set T is a validation set and is provided to validation engine 184 of server machine 180 to perform the validating. In some embodiments, data set T is a testing set and is provided to testing engine 186 of server machine 180 to perform the testing. In the case of a neural network, for example, input values of a given input/output mapping (e.g., numerical values associated with data inputs 301) are input to the neural network, and output values (e.g., numerical values associated with target outputs 303) of the input/output mapping are stored in the output nodes of the neural network. The connection weights in the neural network are then adjusted in accordance with a learning algorithm (e.g., back propagation, etc.), and the procedure is repeated for the other input/output mappings in data set T. After block 414, machine learning model (e.g., machine learning model 190) can be at least one of trained using training engine 182 of server machine 180, validated using validating engine 184 of server machine 180, or tested using testing engine 186 of server machine 180. The trained machine learning model may be implemented by predictive component 114 (of predictive server 112) to generate predictive data 164 for performing corrective action associated with a part of substrate processing equipment 134.

Referring to FIG. 4B, method 400B is associated with training a machine learning model for performing a corrective action associated with a part of substrate processing equipment.

At block 420, processing logic identifies aggregated part-sensor-metrology data associated with a part of substrate processing equipment. The aggregated part-sensor-metrology data may be generated from part data of the part, sensor data of substrate processing operations performed by substrate processing equipment including the part to produce a substrate, and metrology data of the substrate. The sets of aggregated part-sensor-metrology data may be historical data corresponding to parts that have been manufactured and substrates that have been produced.

In some embodiments, at block 422, processing logic identifies performance data corresponding to the aggregated part-sensor-metrology data. In some embodiments, the performance data indicates whether measurements (e.g., dimensions, images, etc.) of the substrates associated with the aggregated part-sensor-metrology data meet threshold measurements (e.g., whether they are good or bad).

At block 424, processing logic trains a machine learning model using data input including the aggregated part-sensor-metrology data (e.g., and target output including the performance data) to generate a trained machine learning model configured to generate outputs to cause performance of a corrective action associated with a part of a substrate processing equipment.

In some embodiments, the machine learning model is trained based on data input (e.g., without target output) to generate an unsupervised trained machine learning model (e.g., to cluster data). In some embodiments, the machine learning model is trained based on data input and target output to generate a supervised trained machine learning model.

Referring to FIG. 4C, method 400C is associated with using a machine learning model for performing a corrective action associated with a part of substrate processing equipment.

At block 440, processing logic receives current data. In some embodiments, the current data is aggregated part-sensor-metrology data for a current part and/or current substrate (e.g., for which there is not performance data). In some embodiments, the current data includes part data, sensor data, and/or metrology data.

At block 442, processing logic provides the current data (e.g., aggregated part-sensor-metrology data) to a trained machine learning model. The trained machine learning model may be trained by method 400B.

At block 444, processing logic obtains, from the trained machine learning model, one or more outputs indicative of predictive data. In some embodiments, the predictive data is predictive performance data (e.g., whether the substrate is good or bad, whether the part is good or bad) (e.g., result from a supervised machine learning model). In some embodiments, the predictive data is an indication of similarity between historical data and the current data (e.g., the historical data and current data are part of the same cluster, the current data is not clustered with any of the historical data) (e.g., result from an unsupervised machine learning model).

At block 446, processing logic causes, based on the predictive data, performance of a corrective action associated with a part of a substrate processing equipment. In some embodiments, the corrective action comprises adjusting part manufacture (e.g., design, dimensions, feature layout, manufacturing operations) or substrate production (e.g., substrate processing operations, hardware of the substrate processing equipment, manufacturing parameters of the substrate processing operations, etc.).

Figure 5:
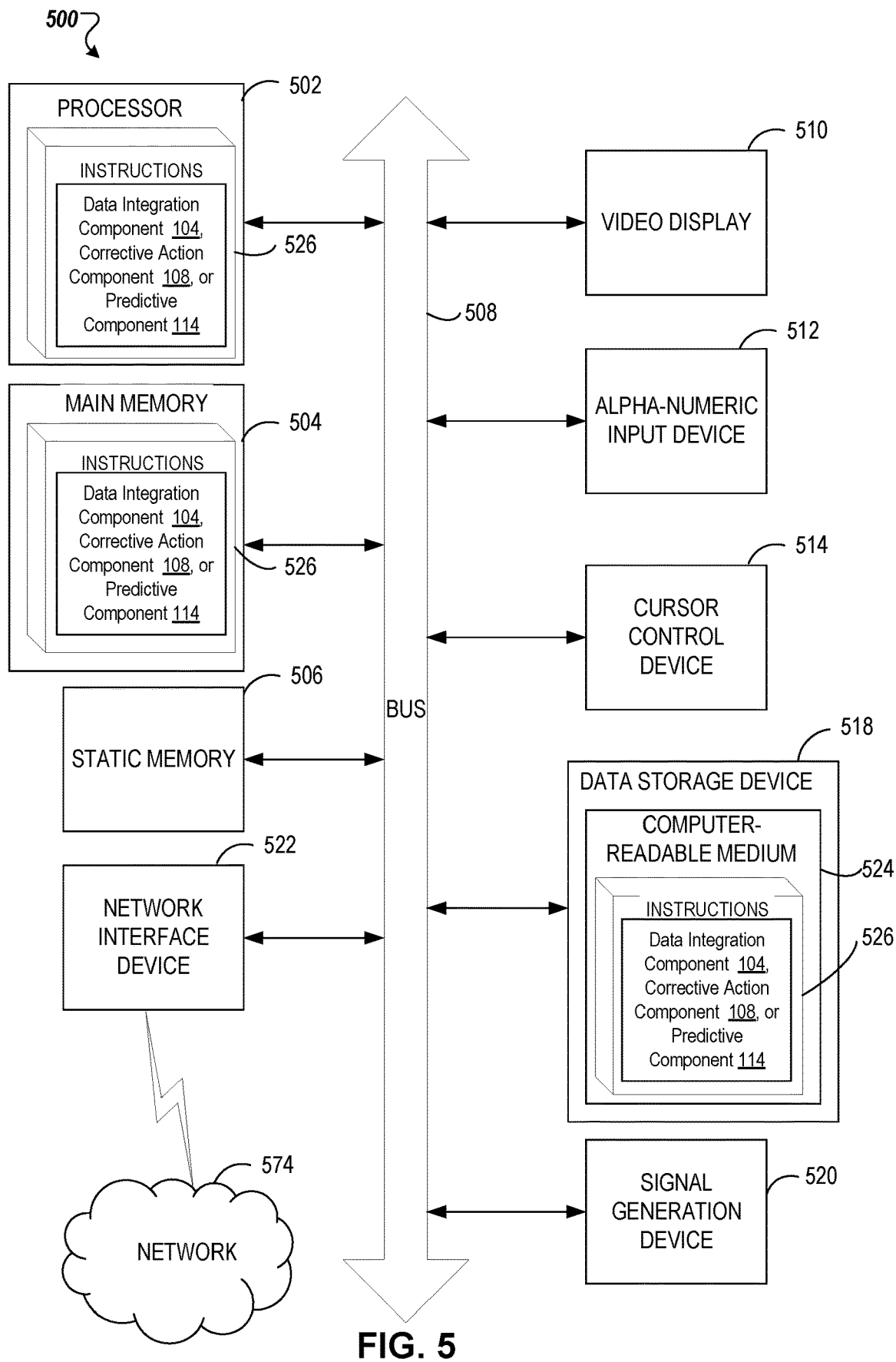
FIG. 5 is a block diagram illustrating a computer system, according to certain embodiments.

FIG. 5 is a block diagram illustrating a computer system 500, according to certain embodiments. In some embodiments, computer system 500 may be connected (e.g., via a network, such as a Local Area Network (LAN), an intranet, an extranet, or the Internet) to other computer systems. Computer system 500 may operate in the capacity of a server or a client computer in a client-server environment, or as a peer computer in a peer-to-peer or distributed network environment. Computer system 500 may be provided by a PC, a tablet PC, a Personal Digital Assistant (PDA), a cellular telephone, a web appliance, a server, a network router, switch or bridge, or any device capable of executing a set of instructions (sequential or otherwise) that specify actions to be taken by that device. Further, the term "computer" shall include any collection of computers that individually or jointly execute a set (or multiple sets) of instructions to perform any one or more of the methods described herein.

In a further aspect, the computer system 500 may include a processing device 502, a volatile memory 504 (e.g., random access memory (RAM)), a non-volatile memory 506 (e.g., read-only memory (ROM) or electrically-erasable programmable ROM (EEPROM)), and a data storage device 516, which may communicate with each other via a bus 508.

Processing device 502 may be provided by one or more processors such as a general purpose processor (such as, for example, a complex instruction set computing (CISC) microprocessor, a reduced instruction set computing (RISC) microprocessor, a very long instruction word (VLIW)

microprocessor, a microprocessor implementing other types of instruction sets, or a microprocessor implementing a combination of types of instruction sets) or a specialized processor (such as, for example, an application specific integrated circuit (ASIC), a field programmable gate array (FPGA), a digital signal processor (DSP), or a network processor).

Computer system 500 may further include a network interface device 522. Computer system 500 also may include a video display unit 510 (e.g., a liquid crystal display (LCD)), an alphanumeric input device 512 (e.g., a keyboard), a cursor control device 514 (e.g., a mouse), and a signal generation device 520.

In some implementations, data storage device 516 may include a non-transitory computer-readable storage medium 524 on which may store instructions 526 encoding any one or more of the methods or functions described herein, including instructions encoding components of FIG. 1 (e.g., data integration component 104, corrective action component 108, predictive component 114, etc.) and for implementing methods described herein.

Instructions 526 may also reside, completely or partially, within volatile memory 504 and/or within processing device 502 during execution thereof by computer system 500, hence, volatile memory 504 and processing device 502 may also constitute machine-readable storage media.

While computer-readable storage medium 524 is shown in the illustrative examples as a single medium, the term "computer-readable storage medium" shall include a single medium or multiple media (e.g., a centralized or distributed database, and/or associated caches and servers) that store the one or more sets of executable instructions. The term "computer-readable storage medium" shall also include any tangible medium that is capable of storing or encoding a set of instructions for execution by a computer that cause the computer to perform any one or more of the methods described herein. The term "computer-readable storage medium" shall include, but not be limited to, solid-state memories, optical media, and magnetic media.

The methods, components, and features described herein may be implemented by discrete hardware components or may be integrated in the functionality of other hardware components such as ASICS, FPGAs, DSPs or similar devices. In addition, the methods, components, and features may be implemented by firmware modules or functional circuitry within hardware devices. Further, the methods, components, and features may be implemented in any combination of hardware devices and computer program components, or in computer programs.

Unless specifically stated otherwise, terms such as "receiving," "generating," "causing," "determining," "updating," "performing," "storing," "training," "interrupting," "selecting," "providing," "displaying," or the like, refer to actions and processes performed or implemented by computer systems that manipulates and transforms data represented as physical (electronic) quantities within the computer system registers and memories into other data similarly represented as physical quantities within the computer system memories or registers or other such information storage, transmission or display devices. Also, the terms "first," "second," "third," "fourth," etc. as used herein are meant as labels to distinguish among different elements and may not have an ordinal meaning according to their numerical designation.

Examples described herein also relate to an apparatus for performing the methods described herein. This apparatus may be specially constructed for performing the methods described herein, or it may include a general purpose computer system selectively programmed by a computer program stored in the computer system. Such a computer program may be stored in a computer-readable tangible storage medium.

The methods and illustrative examples described herein are not inherently related to any particular computer or other apparatus. Various general purpose systems may be used in accordance with the teachings described herein, or it may prove convenient to construct more specialized apparatus to perform methods described herein and/or each of their individual functions, routines, subroutines, or operations. Examples of the structure for a variety of these systems are set forth in the description above.

The above description is intended to be illustrative, and not restrictive. Although the present disclosure has been described with references to specific illustrative examples and implementations, it will be recognized that the present disclosure is not limited to the examples and implementations described. The scope of the disclosure should be determined with reference to the following claims, along with the full scope of equivalents to which the claims are entitled.

What is claimed is:

1. A method comprising:
    receiving a plurality of sets of part data associated with substrate processing equipment, wherein each of the plurality of sets of part data comprises corresponding part values and a corresponding part identifier, and wherein each of the plurality of sets of part data is associated with hardware parameters of a corresponding equipment part of substrate processing equipment;
    receiving a plurality of sets of sensor data, wherein each of the plurality of sets of sensor data comprises corresponding sensor values associated with producing one or more corresponding substrates by the substrate processing equipment and a corresponding sensor data identifier;
    receiving a plurality of sets of metrology data, wherein each of the plurality of sets of metrology data comprises corresponding metrology values associated with the one or more corresponding substrates and a corresponding metrology data identifier;
    generating a plurality of sets of aggregated part-sensor-metrology data, each of the plurality of sets of aggregated part-sensor-metrology data comprising a corresponding set of equipment part data, a corresponding set of sensor data, and a corresponding set of metrology data; and
    causing, based on the plurality of sets of aggregated part-sensor-metrology data, performance of a corrective action associated with the substrate processing equipment, wherein the causing of the performance of the corrective action comprises training a machine learning model using the plurality of sets of aggregated part-sensor-metrology data.

2. The method of claim 1, wherein the plurality of sets of part data comprise one or more of part manufacturing data, part measurement data, or part material property data.

3. The method of claim 1, wherein at least a portion of the plurality of sets of part data are measured via one or more of automated optical inspection (AOI) equipment, an atomic force microscope (AFM), or a coordinate measurement (CMM) machine.

4. The method of claim 1, wherein the plurality of sets of sensor data comprise one or more of pressure data, temperature data, time data, or gas flow data.

5. The method of claim 1, wherein the plurality of sets of metrology data comprise one or more of on-wafer metrology data, imaging data, or thickness data.

6. The method of claim 1, wherein:
each of the plurality of sets of sensor data is associated with one or more corresponding substrate processing operations performed to produce the one or more corresponding substrates; and
each of the plurality of sets of metrology data is associated with the one or more corresponding substrates produced by the one or more corresponding substrate processing operations performed by the substrate processing equipment that comprises the corresponding equipment part.

7. The method of claim 6, wherein the generating of the plurality of sets of aggregated part-sensor-metrology data comprises:
determining common portions between each corresponding part identifier, each corresponding sensor data identifier, and each corresponding metrology data identifier to identify part-sensor-metrology matches; and
for each of the part-sensor-metrology matches, generating a corresponding set of aggregated part-sensor-metrology data that comprises a respective set of part data that corresponds to the corresponding part identifier, a respective set of sensor data that corresponds to the corresponding sensor data identifier, and a respective set of metrology data that corresponds to the corresponding metrology data identifier to generate the plurality of sets of aggregated part-sensor-metrology data.

8. The method of claim 1, wherein the causing of the performance of the corrective action comprises providing the plurality of sets of aggregated part-sensor-metrology data to a trained machine learning model and receiving, from the trained machine learning model, one or more outputs to perform the corrective action.

9. The method of claim 1, wherein the causing of the performance of the corrective action comprises storing the plurality of sets of aggregated part-sensor-metrology data to train a machine learning model to provide a trained machine learning model, and wherein the trained machine learning model is capable of generating one or more outputs to perform the corrective action.

10. The method of claim 6, wherein the performance of the corrective action comprises one or more of:
updating design of the corresponding equipment part;
updating quality of the corresponding equipment part;
updating dimensions of the corresponding equipment part;
updating feature layout of the corresponding equipment part;
updating part manufacturing operations to produce the corresponding equipment part; or
performing root cause analysis to determine updates to the corresponding equipment part or to the one or more corresponding substrate processing operations.

11. A system comprising:
a memory; and a processor, coupled to the memory, to:
receive a plurality of sets of part data associated with substrate processing equipment, wherein each of the plurality of sets of part data comprises corresponding part values and a corresponding part identifier, and wherein each of the plurality of sets of part data is associated with hardware parameters of a corresponding equipment part of substrate processing equipment;
receive a plurality of sets of sensor data, wherein each of the plurality of sets of sensor data comprises corresponding sensor values associated with producing one or more corresponding substrates by the substrate processing equipment and a corresponding sensor data identifier;
receive a plurality of sets of metrology data, wherein each of the plurality of sets of metrology data comprises corresponding metrology values associated with the one or more corresponding substrates and a corresponding metrology data identifier;
generate a plurality of sets of aggregated part-sensor-metrology data, each of the plurality of sets of aggregated part-sensor-metrology data comprising a corresponding set of equipment part data, a corresponding set of sensor data, and a corresponding set of metrology data; and
cause, based on the plurality of sets of aggregated part-sensor-metrology data, performance of a corrective action associated with the substrate processing equipment, wherein the causing of the performance of the corrective action comprises training a machine learning model using the plurality of sets of aggregated part-sensor-metrology data.

12. The system of claim 11, wherein:
the plurality of sets of part data comprise one or more of part manufacturing data, part measurement data, or part material property data; and
at least a portion of the plurality of sets of part data are measured via one or more of automated optical inspection (AOI) equipment, an atomic force microscope (AFM), or a coordinate measurement (CMM) machine.

13. The system of claim 11, wherein to cause the performance of the corrective action, the processor is to provide the plurality of sets of aggregated part-sensor-metrology data to a trained machine learning model and receiving, from the trained machine learning model, one or more outputs to perform the corrective action.

14. The system of claim 11, wherein to cause the performance of the corrective action, the processor is to store the plurality of sets of aggregated part-sensor-metrology data to train a machine learning model to provide a trained machine learning model, and wherein the trained machine learning model is capable of generating one or more outputs to perform the corrective action.

15. A non-transitory computer readable medium having instructions stored thereon, which, when executed by a processing device, cause the processing device to:
receive a plurality of sets of part data associated with substrate processing equipment, wherein each of the plurality of sets of part data comprises corresponding part values and a corresponding part identifier, and wherein each of the plurality of sets of part data is associated with hardware parameters of a corresponding equipment part of substrate processing equipment;
receive a plurality of sets of sensor data, wherein each of the plurality of sets of sensor data comprises corresponding sensor values associated with producing one or more corresponding substrates by the substrate processing equipment and a corresponding sensor data identifier;
receive a plurality of sets of metrology data, wherein each of the plurality of sets of metrology data comprises corresponding metrology values associated with the one or more corresponding substrates and a corresponding metrology data identifier;

generate a plurality of sets of aggregated part-sensor-metrology data, each of the plurality of sets of aggregated part-sensor-metrology data comprising a corresponding set of part data, a corresponding set of sensor data, and a corresponding set of metrology data; and cause, based on the plurality of sets of aggregated part-sensor-metrology data, performance of a corrective action associated with the substrate processing equipment, wherein the causing of the performance of the corrective action comprises training a machine learning model using the plurality of sets of aggregated part-sensor-metrology data.

16. The non-transitory computer readable medium of claim 15, wherein:
the plurality of sets of part data comprise one or more of part manufacturing data, part measurement data, or part material property data; and
at least a portion of the plurality of sets of part data are measured via one or more of automated optical inspection (AOI) equipment, an atomic force microscope (AFM), or a coordinate measurement (CMM) machine.

17. The non-transitory computer readable medium of claim 15, wherein to cause the performance of the corrective action, the processing device is to provide the plurality of sets of aggregated part-sensor-metrology data to a trained machine learning model and receiving, from the trained machine learning model, one or more outputs to perform the corrective action.

* * * * *